(12) United States Patent
Tsuji et al.

(10) Patent No.: US 6,908,940 B2
(45) Date of Patent: Jun. 21, 2005

(54) IMIDAZOLE COMPOUNDS AND THEIR USE AS ADENOSINE DEAMINASE INHIBITORS

(75) Inventors: Kiyoshi Tsuji, Osaka (JP); Tadashi Terasaka, Osaka (JP); Katsuya Nakamura, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 207 days.

(21) Appl. No.: 10/169,757

(22) PCT Filed: Jan. 19, 2001

(86) PCT No.: PCT/JP01/00342

§ 371 (c)(1),
(2), (4) Date: Oct. 22, 2002

(87) PCT Pub. No.: WO01/53271

PCT Pub. Date: Jul. 26, 2001

(65) Prior Publication Data

US 2004/0097571 A1 May 20, 2004

(30) Foreign Application Priority Data

Jan. 19, 2000 (AU) ............................................. PQ5157

(51) Int. Cl.[7] .................. A61K 31/4164; C07D 233/54
(52) U.S. Cl. .................................... 514/400; 548/333.5
(58) Field of Search ....................... 548/333.5; 574/423, 574/400

(56) References Cited

U.S. PATENT DOCUMENTS

| | | | | |
|---|---|---|---|---|
| 5,866,571 A | * | 2/1999 | Niewohner et al. | 514/232.5 |
| 6,124,303 A | * | 9/2000 | Pamukcu et al. | 514/234.2 |
| 6,359,145 B1 | * | 3/2002 | Terasaka et al. | 548/333.5 |
| 6,596,738 B1 | | 7/2003 | Terasaka et al. | |

FOREIGN PATENT DOCUMENTS

| WO | 98 02166 | 1/1998 |
|---|---|---|
| WO | 00 05217 | 2/2000 |
| WO | 00 55155 | 9/2000 |

OTHER PUBLICATIONS

G. Cristalli et al.: "Adenosine deaminase Inhibitors: structure–activity relationships in 1–deazaadenosine and erythro–9–(2–hydroxy–3–nonyl)adenine analogs" Drug Development Research, vol. 28, no. 3, pp. 253–258.

G. Cristalli et al.: "Adenosine deaminase inhibitors: synthesis and structure–activity relationships of imidazole analogues of erythro–9–(2–hydroxy–3–nonyl)adenine" Journal of Medical Chemistry, vol. 34, no. 3, pp. 1187–1192 Mar. 1991.

C. Vargeese et al.: "Adenosine deaminase inhibitors, Synthesis and biological evaluation of putative metabolites of (+)–erythro–9–(2H–hydroxy–3R–nonyl) adenine" Journal of Medical Chemistry, vol. 37, no. 22, pp. 2844–2849 1994.

\* cited by examiner

*Primary Examiner*—Golam M M Shameem
(74) *Attorney, Agent, or Firm*—Oblon, Spivak, McClelland, Maier & Neustadt, P.C.

(57) ABSTRACT

Imidazole compounds having adenosine deaminase inhibitory activity represented by the formula (I) wherein $R^1$ is aryloxy, or aryl which is optionally substituted with suitable substituent(s); $R^2$ is lower alkyl; $R^3$ is hydroxy or protected hydroxy; and -A- is lower alkylene, its prodrug, or their salt. The compounds are useful for treating and/or preventing diseases for which adenosine is effective.

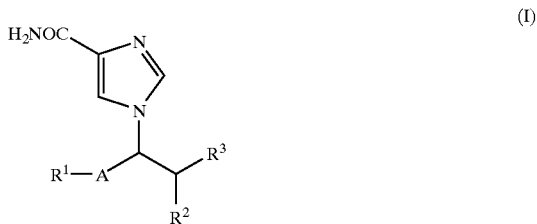

(I)

13 Claims, 10 Drawing Sheets

(1)

(2)

(3)

(4)

2HCl (5)

(6-1)

(6-2)

(7)

(8)

(9)

(10)

(11)

(12)

(13)

(14)

(15)

(16)

(17) HCl

(18) HCl (19)

(20)

(21)

(22)

(23)

(24)

(25)

(26)

(27)

(28)

(29)

(30)

(31)

(32)

(33)

(34)

(35)

(36)

(37)

(38)

(39)

(40)

(41)

(42)

(43)

(44)

(45)

(46)

(47)

(48)

(49)

(50)

(51)

(52)

(53)

(54)

(55)

(56)

(57)

(58)

(59)

(60)

(61)

(62)

(63)

(64)

(65)

(66)

(67)

(68)

(69)

(70)

(71)

(72)

IMIDAZOLE COMPOUNDS AND THEIR USE AS ADENOSINE DEAMINASE INHIBITORS

TECHNICAL FIELD

This invention relates to novel imidazole compounds having pharmacological activity, to a process for their production and to a pharmaceutical composition containing the same.

BACKGROUND ART

Adenosine (Ado) is an endogenous purine nucleoside released by cells as part of the normal metabolic machinery. Ado has wide variety of biological activities, namely potent antiinflammatory and immunosuppressive properties, protective effects in cardiovascular and cerebrovascular ischemia, anticonvulsant effects and modulation effects of platelet aggregation, lipolysis, glycogenesis, blood flow and neurotransmission. Ado shows the biological activities by binding to its receptors anchored in the cell membrane. Therefore, it is the beneficial treatment for many diseases to perform the pharmacological elevation of extracellular Ado concentrations.

Adenosine deaminase (ADA) catalyzes an essentially irreversible deamination of adenosine or deoxyadenosine to inosine or deoxyinosine, respectively. In the last 10 years, ADA, which was considered to be cytosolic, has been found on the cell surface of many cells. Thus, blocking ADA activity with specific inhibitor is the potent way to elevate Ado concentrations in biological systems and the beneficial treatment for many diseases.

Some compounds have been known to have inhibitory activity of ADA (J. Med. Chem. 27, 274–278, 1984; ibid. 31, 390–393, 1988; ibid. 34, 1187–1192, 1991; ibid. 35, 4180–4184, 1992; ibid. 37, 305–308, 1994; ibid. 37, 3844–3849, 1994; and WO98/02166).

Known imidazole compounds with pharmaceutical activity other than ADA inhibitory activity are described in U.S. Pat. No. 4,451,478 and WO97/26883.

Furthermore, some imidazole derivatives having ADA inhibitory activity have been reported, for example, as described in Drug Developement Reseach 28, 253–258, 1993.

DISCLOSURE OF THE INVENTION

This invention relates to novel imidazole compounds, which have pharmaceutical activity such as ADA inhibiting activity, to a process for their production, to a pharmaceutical composition containing the same and to a use thereof.

One object of this invention is to provide the novel imidazole compounds, which have an ADA inhibiting activity.

Another object of this invention is to provide a process for production of the imidazole compounds.

A further object of this invention is to provide a pharmaceutical composition containing the imidazole compound as an active ingredient.

Still further object of this invention is to provide a use of the imidazole compound for manufacturing a medicament for treating or preventing various diseases, or a method of treating or preventing various diseases by administering the imidazole compound in an effective amount to elevate adenosine concentration.

The imidazole compound of this invention can be represented by the following formula (I):

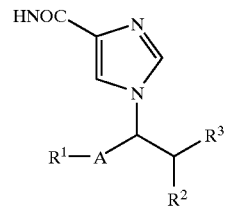

(I)

wherein $R^1$ is aryloxy, or aryl which is optionally substituted with suitable substituent(s);
$R^2$ is lower alkyl;
$R^3$ is hydroxy or protected hydroxy; and
-A- is lower alkylene,
its prodrug, or their salt.

In the compound of formula (I), $R^1$ is preferably aryloxy, or aryl optionally substituted with suitable substituent(s) selected from the group consisting of halogen; hydroxy; aryloxy; lower alkylthio; lower alkylsulfinyl; lower alkylsulfonyl; lower alkylamino; and lower alkoxy substituted with optionally substituted amino, protected amino, halogen, optionally substituted aryl, optionally substituted aryloxy, optionally substituted arylthio, optionally substituted arylsulfinyl, optionally substituted arylsulfonyl, optionally substituted aryl(lower)alkoxy, or optionally substituted heterocyclic group. More preferably, $R^3$ is naphthyloxy; phenyl substituted with substituent(s) selected from the group consisting of halogen, hydroxy, aryloxy, lower alkylthio, lower alkylsulfinyl, lower alkylsulfonyl, lower alkylamino, and lower alkoxy substituted with optionally substituted amino, protected amino, halogen, optionally substituted aryl, optionally substituted aryloxy, optionally substituted arylthio, optionally substituted arylsulfinyl, optionally substituted arylsulfonyl, optionally substituted aryl(lower)alkoxy, or optionally substituted heterocyclic group; or naphthyl substituted with halogen. A is preferably ethylene.

The compound (I), its prodrug, or their salt can be prepared by the following processes. In the following formulae, compounds may be prodrugs or their salts.

Process 1

The compound (I) wherein $R^3$ is not hydroxy can be obtained by reacting a compound of formula (III)

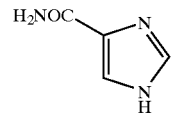

(III)

with a compound of formula (IV)

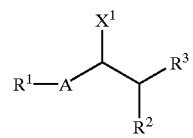

(IV)

wherein $R^1$, $R^2$, $R^3$, and A are as defined above, and $X^1$ is hydroxy or a leaving group (such as halogen, alkanesulfonyloxy, arylsulfonyloxy, and the like), provided that $R^3$ is not hydroxy;

In this process the compound (I) can be produced by reacting the compound (IV), where $X^1$ is hydroxy, with alkanesulfonyl chloride (i.e., methanesulfonyl chloride, etc.) or arylsulfonyl chloride (i.e. toluenesulfonyl chloride, etc.) in the presence of a base such as triethylamine or pyridine in a solvent, which does not adversely affect the reaction, such as dichloromethane, chloroform, tetrahydrofuran, or diethyl ether from 0° C. to room temperature for about 1 hour and reacting the resulting sulfonate with the compound (III) in the presence of a base such as sodium hydride, potassium tert-butoxide, or potassium carbonate in a solvent such as dimethylformamide (DMF) from room temperature to 100° C. Alternatively, the compound (III) can be reacted with the compound (IV) in the presence of a base such as sodium methoxide, potassium tert-butoxide, or sodium hydride to give the compound (I).

Process 2

The compound (I) wherein $R^3$ is not hydroxy can also be obtained by reacting a compound of formula (V)

wherein $R^1$ is as defined above, with a compound of formula (VI)

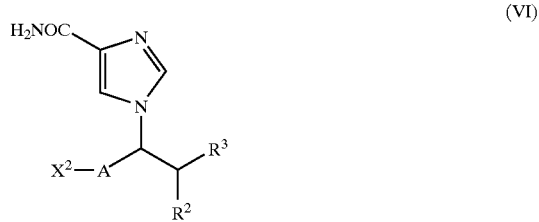

wherein $R^2$, $R^3$, and A are as defined above, and $X^2$ is hydroxy or a leaving group, provided that $R^3$ is not hydroxy.

The reaction may be carried out in a manner such as the Mitsunobu reaction or the modification thereof. This reaction can be preferably carried out in the presence of di(lower)alkyl azodicarboxylate (e.g., diethyl azodicarboxylate, etc.) and trialkyl or triarylphosphines (e.g., triphenylphosphine, etc.) in a solvent, which does not adversely affect the reaction, such as tetrahydrofuran, diethylether, or the like. The reaction temperature is not critical and the reaction is usually carried out under cooling to warming.

This reaction may also be carried out in a similar manner to Process 1.

Process 3

The compound (I) wherein $R^3$ is hydroxy can be obtained by reacting a compound of formula (I-1)

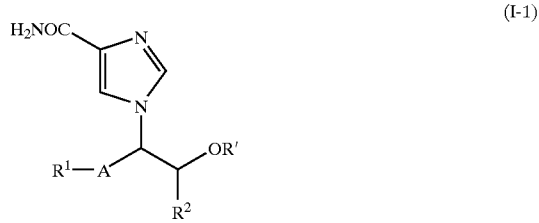

wherein $R^1$, $R^2$, and A are as defined above, and R' is hydroxy protective group, with a deprotecting agent.

The compound (I-1) can be reacted with a deprotecting agent such as palladium hydroxide on carbon/cyclohexane, iodotrimethylsilane or tetrabutylammonium fluoride in a solvent, which does not adversely affect the reaction, such as ethanol, chloroform or tetrahydrofuran. The reaction temperature is not critical and the reaction is usually carried out under cooling to warming.

Process 4

The compound (I) that is represented by formula (IX)

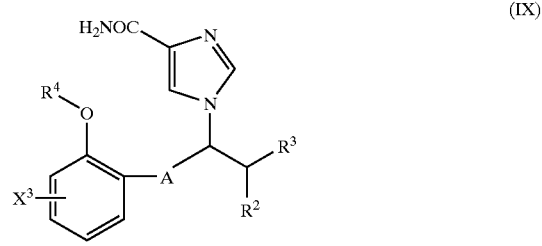

wherein $R^2$ and $R^3$ are as defined above, $X^3$ is hydrogen or halogen, and $R^4$ is lower alkyl substituted with optionally substituted amino, protected amino, halogen, optionally substituted aryl, optionally substituted aryloxy, optionally substituted arylthio, optionally substituted arylsulfinyl, optionally substituted arylsulfonyl, optionally substituted aryl(lower)alkoxy, or optionally substituted heterocyclic group; wherein substituent(s) of the optionally substituted amino, optionally substituted aryl, optionally substituted aryloxy, optionally substituted arylthio, optionally substituted arylsulfinyl, optionally substituted arylsulfonyl, optionally substituted aryl(lower)alkoxy, and optionally substituted heterocyclic group, are each independently selected from the group consisting of aryl optionally substituted with halogen, lower alkyl or halo(lower)alkyl; halogen; aryloxy optionally substituted with halogen; aryl (lower)alkyl; heterocyclic group optionally substituted with cyano; aryloxy(lower)alkyl; aryl(lower)alkenyl; arylthio; lower cycloalkyl; lower alkylthio; heterocyclicthio optionally substituted with halogen; lower alkoxy; cyano; lower alkyl; halo(lower)alkyl; and amino optionally substituted with lower alkyl or lower alkanoyl; can be obtained by reacting a compound of formula (VII)

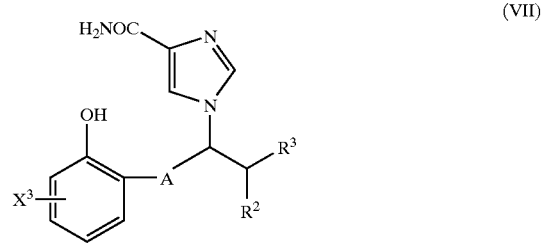

wherein $R^2$, $R^3$, and $X^3$ are as defined above, with a compound of formula (VIII)

wherein $R^4$ is as defined above and $X^4$ is a leaving group.

The reaction can be carried out in the presence of a base such as potassium carbonate in a solvent, which does not adversely affect the reaction, such as N,N-dimethylformamide from 0° C. to 150° C. for 1 hour to 72 hours.

In the following, suitable examples of the definitions to be included within the scope of the invention are explained in detail.

The term "lower" means a group having 1 to 6 carbon atom(s), unless otherwise provided.

Suitable "lower alkyl" and lower alkyl moiety of "lower alkoxy," "lower alkylthio," "lower alkylsulfinyl," "lower alkylsulfonyl," "lower alkylamino," "halo(lower)alkyl," "aryl(lower)alkyl," "aryl(lower)alkoxy," "aryloxy(lower) alkyl," and "lower alkanoyl" include a straight or branched one such as methyl, ethyl, propyl, isopropyl, butyl, isobutyl, tert-butyl, pentyl, hexyl, or the like, with methyl being preferred.

Suitable "lower cycloalkyl" includes one having 3 to 8 carbon atoms, such as cyclopropyl, cyclobutyl, cyclopentyl, cyclohexyl, or the like, with cyclohexyl being preferred.

Suitable "lower alkenyl" and lower alkenyl moiety of "aryl(lower)alkenyl" include a straight or branched one such as ethenyl, allyl, 1-propenyl, isopropenyl, 1-butenyl, 2-butenyl, 2-pentenyl, or the like, with ethenyl being preferred.

Suitable "lower alkylene" may be straight or branched one having 1 to 8 carbon atom(s), such as methylene, ethylene, trimethylene, tetramethylene, pentametylene, hexamethylene, or the like, with ethylene being preferred.

Suitable "halogen" and halogen moiety of "haloaryl" and "halo(lower)alkyl" include fluorine, chlorine, bromine, or iodine.

Suitable "aryl" and aryl moiety of "aryloxy," "haloaryl," "arylthio," "arylsulfinyl," "arylsulfonyl," "aryl(lower) alkyl," "aryl(lower)alkoxy," "aryloxy(lower)alkyl," and "aryl(lower)alkenyl" include phenyl, naphthyl, tolyl, xylyl, or the like, with phenyl and naphthyl being preferred.

Suitable "protectedamino" includes (lower) alkoxycarbonylamino such as methoxycarbonylamino, ethoxycarbonylamino, 2,2,2-trichloroethoxycarbonylamino, 2-trimethylsilylethoxycarbonylamino, 2-phenylethoxycarbonylamino, t-butoxycarbonylamino, allyloxycarbonylamino, or the like; acylamino such as formylamino, acetylamino, trichloroacetylamino, benzoylamino, phthalimidoamino, or the like.

Suitable amino protective groups in the protected amino group include (lower)alkoxycarbonyl such as methoxycarbonyl, ethoxycarbonyl, 2,2,2-trichloroethoxycarbonyl, 2-trimethylsilylethoxycarbonyl, 2-phenylethoxycarbonyl, t-butyoxycarbonyl, allyloxycarbonyl, or the like and acyl such as formyl, acetyl, trichloroacetyl, benzoyl, phthalimido, or the like.

Suitable "lower alkylamino" includes mono(lower) alkylamino and di(lower)alkylamino, such as methylamino, dimethylamino, ethylamino, diethylamino, or the like.

Suitable "heterocyclic group" and heterocyclic group moiety of "heterocyclicthio" include one containing at least one heteroatom selected from the group consisting of nitrogen, sulfur, and oxygen atom, and include saturated or unsaturated, monocyclic or polycyclic heterocyclic group such as:

(1) unsaturated, 3 to 7-membered, preferably 5 or 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.], tetrazolyl [e.g., 1H-tetrazolyl, 2H-tetrazolyl, etc.], etc.;

(2) saturated, 3 to 7-membered, preferably 5 or 6-membered heteromonocyclic group containing 1 to 4 nitrogen atoms, for example, pyrrolidinyl, imidazolidinyl, piperidino, piperazinyl, etc.;

(3) unsaturated, condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.;

(4) unsaturated, 3 to 7-membered, preferably 5 or 6-membered heteromonocyclic group containing an oxygen atom, for example, pyranyl, furyl, etc.;

(5) unsaturated, 3 to 7-membered, preferably 5 or 6-membered heteromonocyclic group containing 1 to 2 sulfur atoms, for example, thienyl, etc.;

(6) unsaturated, 3 to 7-membered, preferably 5 or 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.], etc.;

(7) saturated, 3 to 7-membered, preferably 5 or 6-membered heteromonocyclic group containing 1 to 2 oxygen atoms and 1 to 3 nitrogen atoms, for example, morpholinyl, etc.;

(8) unsaturated, condensed heterocyclic group containing 1 to 2 oxygen atoms and 1 to 3 nitrogen atoms, for example, benzoxazolyl, benzoxadiazolyl, etc.;

(9) unsaturated, 3 to 7-membered, preferably 5 or 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.;

(10) saturated, 3 to 7-membered, preferably 5 or 6-membered heteromonocyclic group containing 1 to 2 sulfur atoms and 1 to 3 nitrogen atoms, for example, thiazolidinyl, etc.;

(11) unsaturated, condensed heterocyclic group containing 1 to 2 sulfur atoms and 1 to 3 nitrogen atoms, for example, benzothiazolyl, benzothiadiazolyl, etc.;

(12) unsaturated, condensed heterocyclic group containing 1 to 2 sulfur atoms or 1 to 2 oxygen atoms, for example, benzothiophen, benzofuran, etc.; or the like.

Among the above, more preferable "heterocyclic group" is unsaturated heteromonocyclic group such as abovementioned (1), (4), (5), (6), and (9), in which most preferable one is pyrrolyl (e.g., 1-pyrrolyl), pyridyl (e.g., 2-pyridyl), thienyl (e.g., 2-thienyl and 3-thienyl), oxadiazolyl (e.g., 1,2,4-oxadiazol-3-yl), thiazolyl (e.g., 2-thiazolyl), orthiadiazolyl (e.g., 1,2,3-thiadiazol-4-yl).

Suitable "protected hydroxy" includes lower alkoxy optionally substituted with aryl; acyloxy; or tri(lower) alkylsilyloxy (i.e., trimethylsilyloxy, tert-butyldimethylsilyloxy, etc.); or the like.

Suitable hydroxy protective groups in the protected hydroxy group include lower alkyl optionally substituted with aryl; acyl; tri(lower)alkylsilyl (i.e., trimethylsilyl, tert-butyldimethyl-silyl, etc.); or the like. Here, suitable "acyl" includes acetyl, trifluoroacetyl, or the like.

Suitable "leaving group" includes halogen, acyloxy (e.g., acetyloxy, trifluoroacetyloxy, etc.), lower alkylsulfonyloxy (e.g., methanesulfonyloxy, etc.), triarylphosphinoxy (e.g., —O—P$^+$(C$_6$H$_5$)$_3$, etc.), or the like.

Suitable substituent(s) of "optionally substituted amino," "optionally substituted aryl," "optionally substituted aryloxy," "optionally substituted arylthio," "optionally substituted arylsulfinyl," "optionally substituted arylsulfonyl," "optionally substituted aryl(lower)alkoxy," and "optionally substituted heterocyclic group," each independently include aryl optionally substituted with halogen, lower alkyl or halo(lower)alkyl; halogen; aryloxy optionally substituted with halogen; aryl(lower)alkyl; heterocyclic group optionally substituted with cyano; aryloxy(lower)alkyl; aryl (lower)alkenyl; arylthio; lower cycloalkyl; lower alkylthio; heterocyclicthio optionally substituted with halogen; lower alkoxy; cyano; lower alkyl; halo(lower)alkyl; amino optionally substituted with lower alkyl or lower alkanoyl, or the like.

Suitable "optionally substituted amino" includes unsubstituted amino, lower alkylamino (e.g., methylamino, dimethylamino, etc.) or the like.

The term "optionally substituted aryl" means aryl which is optionally substituted with one or more substituent(s) selected from halogen, optionally substituted aryloxy, lower alkylthio, lower alkoxy, aryl, aryl(lower)alkyl, optionally substituted heterocyclic group, aryloxy(lower)alkyl, aryl (lower)alkenyl, arylthio, lower cycloalkyl, optionally substituted heterocyclicthio, cyano, halo(lower)alkyl, lower alkyl, and the like.

Examples of the "optionally substituted aryl" include unsubstituted aryl such as phenyl, naphthyl, or the like; haloaryl such as 3-fluorophenyl, 4-fluorophenyl, 4-chlorophenyl, 2,3-dichlorophenyl, 3,4-dichlorophenyl, 3-bromophenyl, 4-bromophenyl, 3,5-dibromophenyl, 4-bromo-2-fluorophenyl, 6-chloro-1-naphthyl, 7-chloro-1-naphthyl, or the like; aryl substituted with aryloxy which may be substituted with halogen, such as phenoxyphenyl, 4-fluorophenoxyphenyl, or the like; lower alkylthioaryl such as 2-(methylthio)phenyl, 4-(methylthio)phenyl, or the like; lower alkoxyaryl such as 4-methoxyphenyl, 3,5-dimethoxyphenyl, 4-ethoxyphenyl, or the like; arylaryl such as 4-biphenylyl or the like; aryl(lower)alkylaryl such as 4-(1-methyl-1-phenylethyl)phenyl or the like; aryl substituted with heterocyclic group which may be substituted with cyano, such as 4-(2-thienyl)phenyl, 4-(2-pyridyl)phenyl, 4-(1,2,3-thiadiazol-4-yl)phenyl, 4-(2-cyano-1-pyrrolyl) phenyl, or the like; aryloxy(lower)alkylaryl such as 3-(phenoxymethyl)phenyl or the like; aryl(lower) alkenylaryl such as 4-styrylphenyl or the like; arylthioaryl such as 4-(phenylthio)phenyl or the like; lower cycloalkylaryl such as 4-cyclohexylphenyl or the like; aryl substituted with heterocyclicthio which may be substituted with halogen, such as 4-(2-thienylthio)phenyl, 4-(5-chloro-2-thienylthio)phenyl, or the like; cyanoaryl such as 4-cyanophenyl or the like; halo(lower)alkylaryl such as 3,5-bis(trifluoromethyl)phenyl or the like; and lower alkylaryl such as 4-isopropylphenyl, 3,5-dimethylphenyl, or the like.

Suitable "optionally substituted aryloxy" includes unsubstitutedaryloxy such as phenoxy, 1-naphthyloxy, 2-naphthyloxy, or the like; arylaryloxy such as 4-biphenylyloxy or the like; and haloaryloxy such as 4-fluorophenoxy, 4-chlorophenoxy, or the like.

Suitable "optionally substituted arylthio" includes unsubstituted arylthio such as phenylthio or the like and haloarylthio such as 4-chlorophenylthio or the like.

Suitable "optionally substituted arylsulfinyl" includes unsubstituted arylsulfinyl such as phenylsulfinyl or the like and haloarylsulfinyl such as 4-chlorophenylsulfinyl or the like.

Suitable "optionally substituted arylsulfonyl" includes unsubstituted arylsulfonyl such as phenylsulfonyl or the like and haloarylsulfonyl such as 4-chlorophenylsulfonyl or the like.

Suitable "optionally substituted aryl(lower)alkoxy" includes unsubstituted aryl(lower)alkoxy such as benzyloxy, 1-naphthylmethyloxy, 2-naphthylmethyloxy, or the like; haloaryl(lower)alkoxy such as 3,4-dichlorobenzyloxy or the like.

Suitable "optionally substituted heterocyclic group" includes unsubstituted heterocyclic group; heterocyclic group substituted with aryl which may be substituted with halogen, lower alkyl, or halo(lower)alkyl, such as 5-(4-tert-butylphenyl)-1,2,4-oxadiazol-3-yl, 2-(4-(trifluoromethyl)phenyl)-4-thiazolyl, 5-(4-fluorophenyl)-2-thienyl, or the like; heterocyclic group substituted with amino which may be substituted with lower alkyl and/or lower alkanoyl, such as 2-(N-methylpropionylamino)-4-thiazolyl or the like; heterocyclic group substituted with heterocyclic group, such as 4-(3-thienyl)-2-thienyl or the like; heterocyclic group substituted with heterocyclicthio, such as 5-(2-thiazolylthio)-2-thienyl or the like; heterocyclic group substituted with halogen, such as 5-bromo-2-thienyl or the like.

Suitable salts of the compounds of the present invention are pharmaceutically acceptable conventional non-toxic salts and can be an organic acid addition salt (e.g. formate, acetate, trifluoroacetate, maleate, tartarate, oxalate, methanesulfonate, benzenesulfonate, toluenesulfonate, etc.), an inorganic acid addition salt (e.g. hydrochloride, hydrobromide, sulfate, phosphate, etc.), a salt with an amino acid (e.g. aspartic acid salt, glutamic acid salt, etc.) or the like.

The "prodrug" means the derivatives of compounds of the present invention having a chemically or metabolically degradable group, which becomes pharmaceutically active after biotransformation.

The compounds of formula (I) may contain one or more asymmetric centers and thus they can exist as enantiomers or diastereoisomers. Furthermore certain compounds of formula (I) which contain alkenyl groups may exist as cis- or trans-isomers. In each instance, the invention includes both mixtures and separate individual isomers.

The compounds of the formula (I) may also exist in tautomeric forms and the invention includes both mixtures and separate individual tautomers.

The compound of the formula (I) and its salt can be in a form of a solvate, which is included within the scope of the present invention. The solvate preferably include a hydrate and an ethanolate.

Also included in the scope of invention are radiolabelled derivatives of compounds of formula (I) which are suitable for biological studies.

The compound of the present invention can be purified by any conventional purification methods employed for purifying organic compounds, such as recrystallization, column chromatography, thin-layer chromatography, high-performance liquid chromatography and the like. The compound scan be identified by conventional methods such as NMR spectrography, mass spectrography, IR spectrography, elemental analysis, and measurement of melting point.

The compound (I), its prodrug, or their salt can be administered alone or in the form of a mixture, preferably, with a pharmaceutical vehicle or carrier.

The active ingredient of this invention can be used in the form of a pharmaceutical preparation, for example, in solid, semisolid or liquid form, which contains a compound (I), as an active ingredient, in admixture with an organic or inorganic carrier or excipient suitable for oral, external (topical), enteral, intravenous, intramuscular, parenteral or intramucous applications. The active ingredient can be formulated, for example, with the conventional non-toxic, pharmaceutically acceptable carriers for ointment, cream, plaster, tablets, pellets, capsules, suppositories, solution (saline, for example), emulsion, suspension (olive oil, for example), aerosols, pills, powders, syrups, injections, troches, cataplasms, aromatic waters, lotions, buccal tablets, sublingual tablets, nasal drops and any other form suitable for use. The carriers which can be used are water, wax, glucose, lactose, gum acacia, gelatin, mannitol, starch paster, magnesium trisilicate, talc, cornstarch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in a pharmaceutical composition in an effective amount sufficient to produce the desired effect upon the process or condition of the diseases.

The active ingredient can be formulated into, for example, preparations for oral application, preparations for injection, preparations for external application, preparations for inhalation, preparations for application to mucous membranes.

Mammals which may be treated by the present invention include livestock mammals such as cows, horses, etc., domestic animals such as dogs, cats, rats, etc. and humans, preferably humans.

While the dosage of therapeutically effective amount of the compound (I) will vary depending upon the age and condition of each individual patient, an average single dose to a human patient of about 0.01 mg, 0.1 mg, 1 mg, 10 mg, 50 mg, 100 mg, 250 mg, 500 mg, and 1000 mg of the compound (I) may be effective for treating the above-mentioned diseases. In general, amounts between 0.01 mg/body and about 1,000 mg/body may be administered per day.

An ADA inhibitor, such as the compound (I) or its pharmaceutically acceptable salts of this invention, possesses ADA inhibiting activity and are thus useful in immunomodulation, especially immunosuppression, antiinflammation and treatment and prevention of various diseases for which Ado is effective. Examples of the diseases are as follows:

a) Autoimmune diseases and inflammatory conditions, e.g., various pains collagen diseases, autoimmune diseases, various immunity diseases, and the like in human beings or animals, and more particularly for the treating and/or preventing inflammation and pain in joint and muscle (e.g. rheumatoid arthritis, rheumatoid spondylitis, osteoarthritis, gouty arthritis, etc.), inflammatory skin condition (e.g. sunburn, eczema, etc.), inflammatory eye condition (e.g. conjunctivitis, etc.), lung disorder in which inflammation is involved (e.g. asthma, bronchitis, pigeon fancier's disease, farmer's lung, etc.), condition of the gastrointestinal tract associated with inflammation (e.g. aphthous ulcer, Crohn's disease, atrophic gastritis, ulcerative colitis, coeliac disease, regional ileitis, irritable bowel syndrome, etc.), gingivitis, (inflammation, pain and tumescence after operation or injury), pyrexia, pain and other conditions associated with inflammation, systemic lupus erythematosus, scleroderma, polymyositis, polychondritis, periarteritis nodosa, ankylosing spondylitis, inflammatory chronic renal condition (e.g. nephrotic syndrome, glomerulonephritis, membranous nephritis, etc.), acute nephritis, rheumatic fever, Sjogren's syndrome, Behcet disease, thyroiditis, type I diabetes, dermatomyositis, chronic active hepatitis, acute hepatitis, myasthenia gravis, idiopathic sprue, Grave's disease, multiple sclerosis, primary billiary cirrhoris, Reiter's syndrome, autoimmune hematological disorders (e.g. hemolytic anemia, pure red cell anemia, idiopathic thrombocytopenia; aplastic anemia, etc.), myasthenia gravis, uveitis, contact dermatitis, psoriasis, Kawasaki disease, sarcoidosis, Wegner's granulomatosis, Hodgkin's disease, or the like;

b) Organ or tissue allo-or xeno-transplant rejection, e.g., kidney, liver, heart, lung, combined heart-lung, bone marrow, islet cells, pancreatic, skin, chromaffin or dopamine producing cells, small bowel, or corneal transplantation. Treating and/or preventing graft-versus-host disease, such as occurs following bone marrow transplantation;

c) Chronic pain (e.g., cancer pain, diabetic neuropathy, etc);

d) Various leukemias, including virus induced, or various induced lymphomas; and e) Diseases that arise from, or are aggravated by, insufficient blood flow through a particular organ or portion thereof, e.g., heart attacks or strokes, the microvascular disease of diabetes mellitus, atherosclerosis, or events resulting in a less prolonged loss of blood flow (e.g., angina pectoris, transient ischemic attacks, bowel ischemia, kidney ischemia, intermittent claudication of skeletal muscle, migraine headaches, Raynaud's phenomenon), or the like.

An ADA inhibitor, such as the compound (I) or its pharmaceutically acceptable salt of this invention, is useful for protection against the progression of glomerulosclerosis by suppressing glomerular hypertension and hyperfiltration, and thus useful for treatment and/or prevention of glomerulosclerosis.

An ADA inhibitor, such as the compound (I) or its pharmaceutically acceptable salt of this invention, is useful for complementing the defect of an IL-2 inhibitor, such as FK506, cyclosporin, or the like, in immunosupresive effects. Thus, the combination use of the two compounds enables treatment and prevention of various diseases and conditions in need of immunosuppression.

Any patents, patent applications, and publications cited herein are incorporated by reference.

In order to illustrate the usefulness of the object compound (I), the pharmacological test data of the compound (I) are shown in the following.

Adenosine Deaminase (ADA) Enzyme Assay

Test Compound:

1-{(2S,3R)-2-hydroxy-5-[2-(3-(4-chlorophenyl)propoxy)-phenyl]-3-pentyl}imidazole-4-carboxamide (Example 8)

1-[(2S,3R)-2-hydroxy-5-(7-chloro-1-naphthyl)-3-pentyl]-imidazole-4-carboxamide (Example 12)

Test Method:

The reaction velocity (V) is measured by a change in absorbance at 265 nm (A265) resulting from the deamination of adenosine. Human ADA was expressed and purified from ADA-deficient bacterial strain. Reaction mixtures of a total volume of 200 $\mu$l contained 0.16 $\mu$g/ml of ADA and 0.1 mM of adenosine and test compound in 10 mM phosphate buffer saline (pH 7.4). The reaction was started by addition of ADA to a mixture of adenosine and test compound. The reaction was followed at room temperature by recording decrease in A265 for 3 minutes in SPECTRAmax 250 (Molecular Devices, USA) to automatically calculate $V_{max}$. Inhibitory potency of test compound was expressed as $IC_{50}$ value, the drug concentration required to produce 50% inhibition of $V_{max}$ in comparison to vehicle treatment.

| Results: | |
| --- | --- |
| Test Compound | $IC_{50}$ (nM) |
| Example 8 | <20 |
| Example 12 | <20 |

BEST MODE FOR CARRYING OUT THE INVENTION

Figure 1:
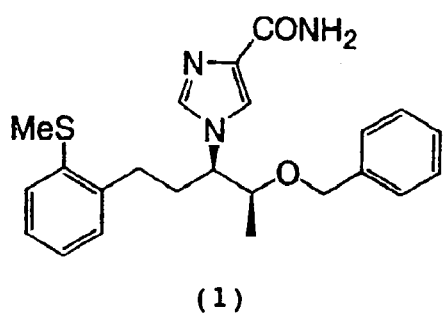
FIG. 1 shows chemical formulae of compound (1) to compound (5) and compound (6-1).
Figure 1:
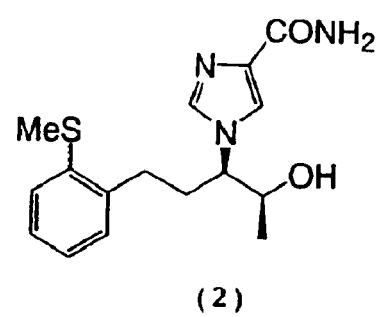
Figure 1:
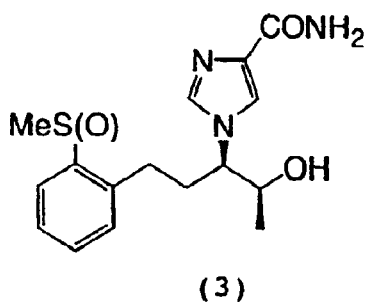
Figure 1:
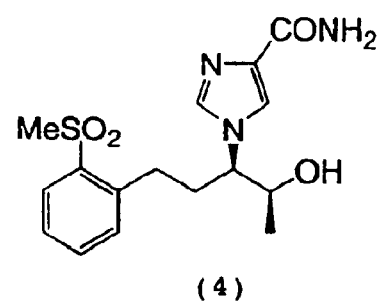
Figure 1:
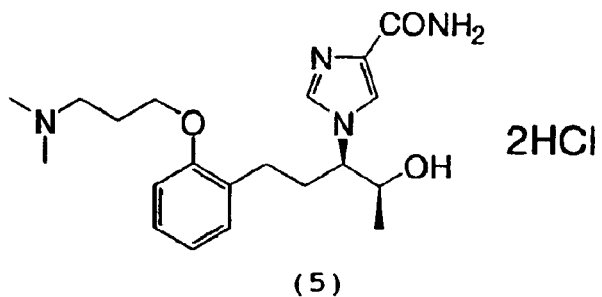
Figure 1:
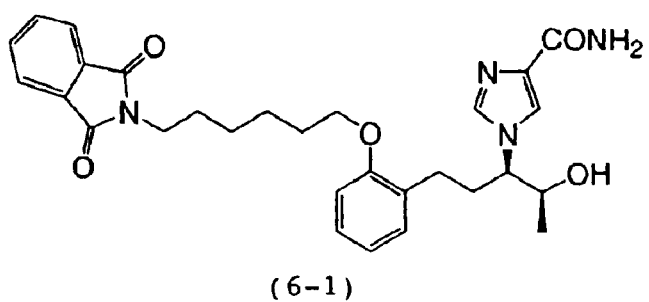
Figure 2:
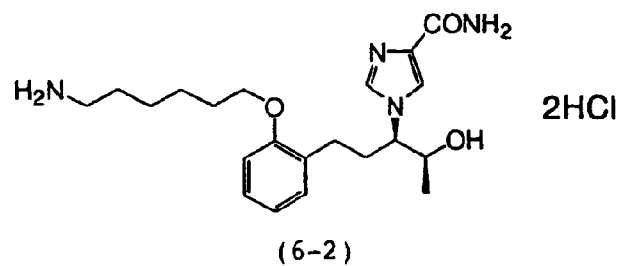
FIG. 2 shows chemical formulae of compound (6-2) and compound (7) to compound (12).
Figure 2:
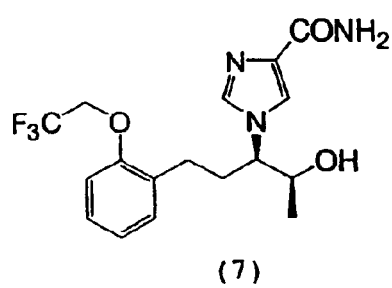
Figure 2:
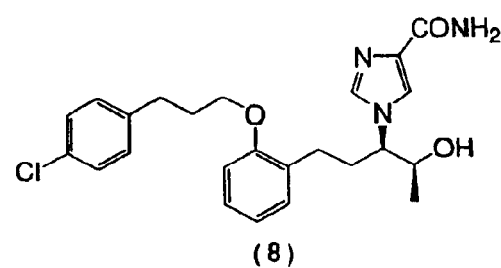
Figure 2:
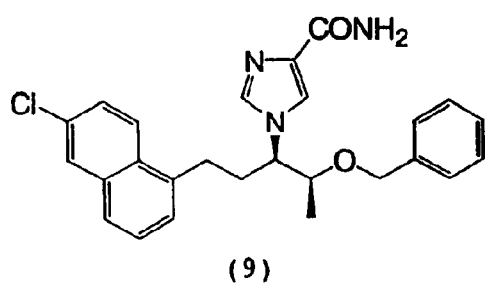
Figure 2:
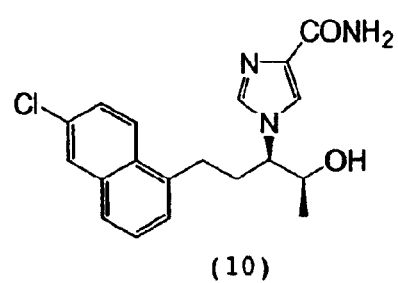
Figure 2:
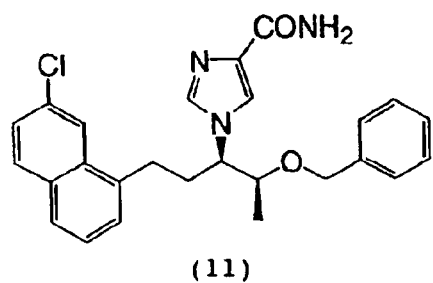
Figure 2:
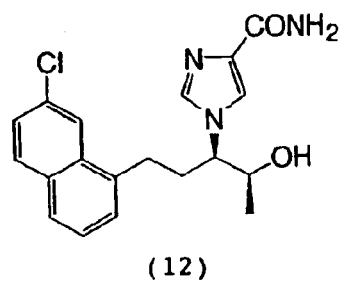
Figure 3:
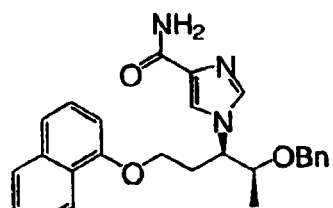
FIG. 3 shows chemical formulae of compound (13) to compound (20).
Figure 3:
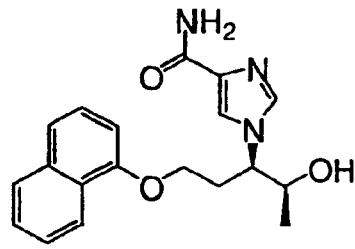
Figure 3:
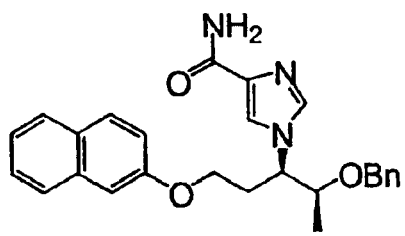
Figure 3:
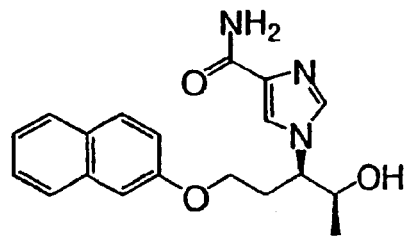
Figure 3:
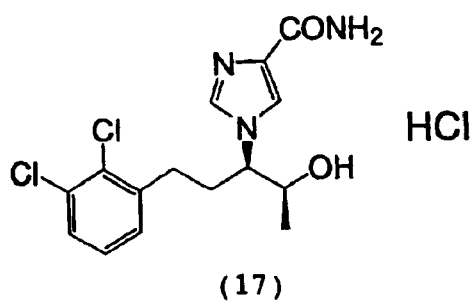
Figure 3:
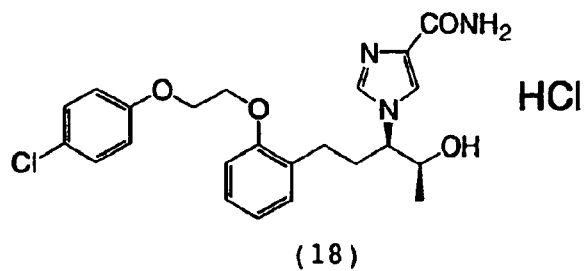
Figure 3:
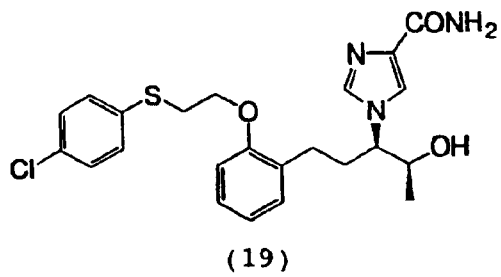
Figure 3:
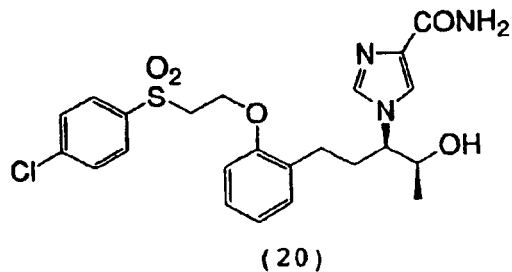
Figure 4:
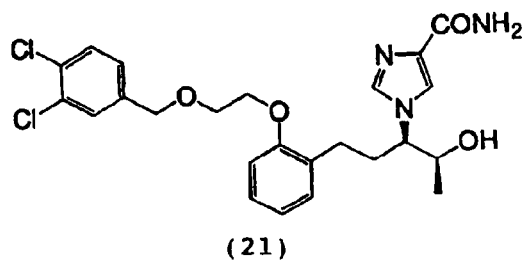
FIG. 4 shows chemical formulae of compound (21) to compound (28).
Figure 4:
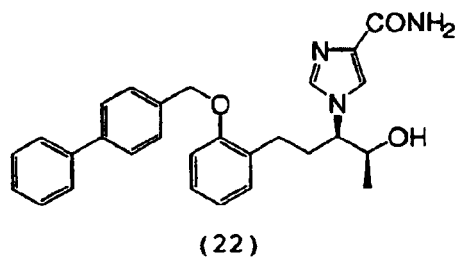
Figure 4:
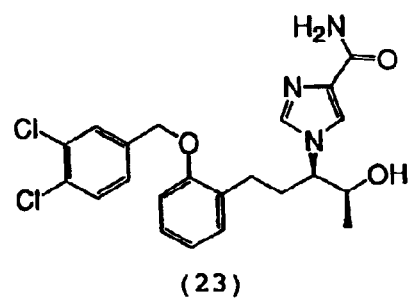
Figure 4:
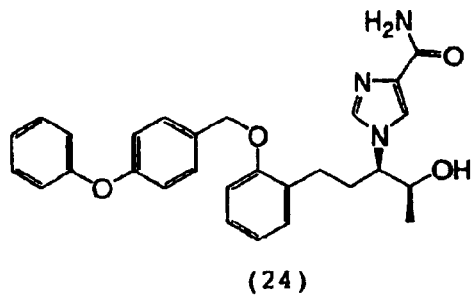
Figure 4:
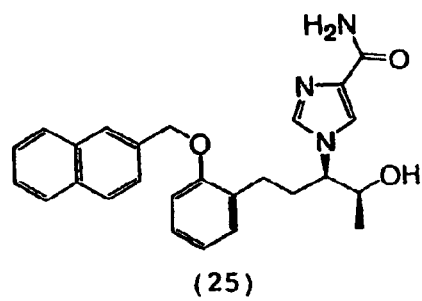
Figure 4:
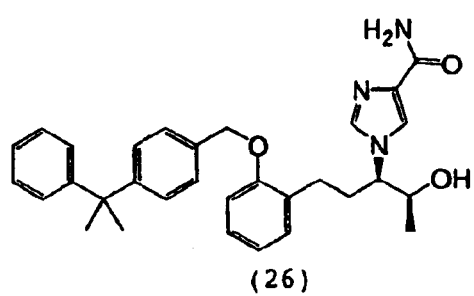
Figure 4:
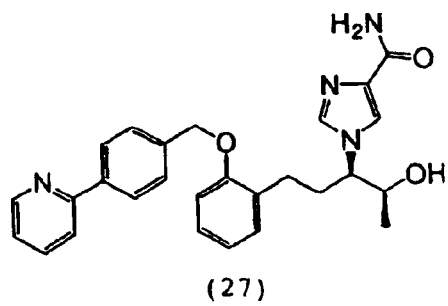
Figure 4:
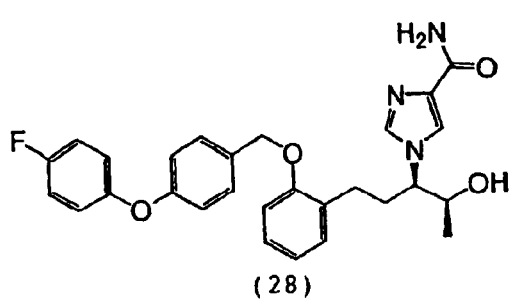
Figure 5:
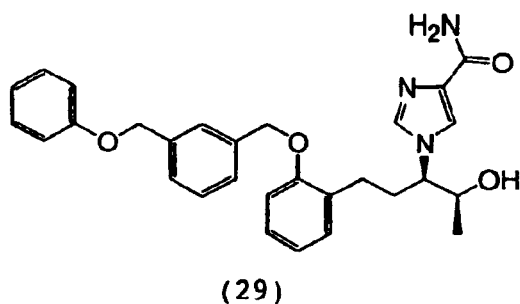
FIG. 5 shows chemical formulae of compound (29) to compound (36).
Figure 5:
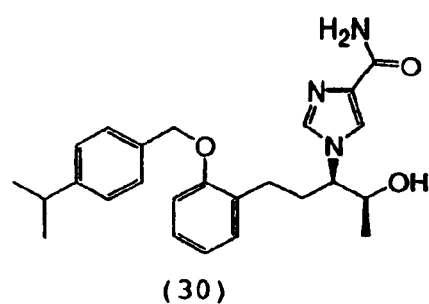
Figure 5:
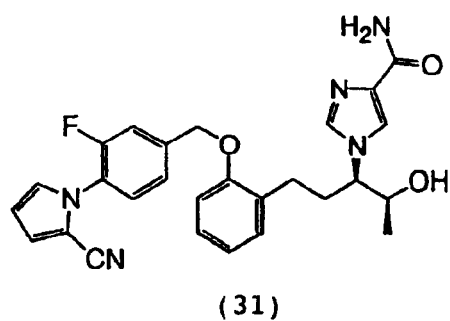
Figure 5:
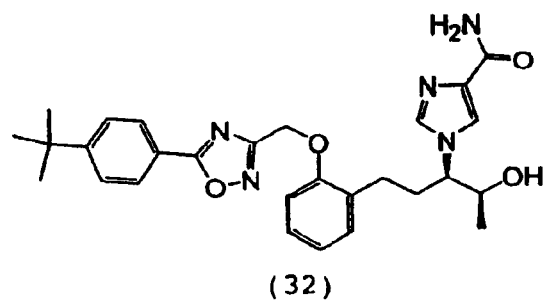
Figure 5:
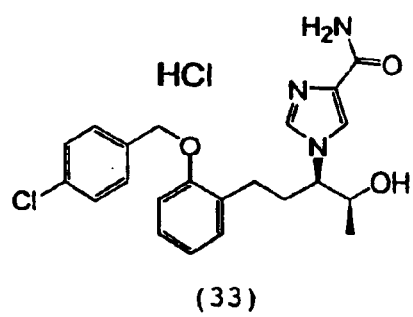
Figure 5:
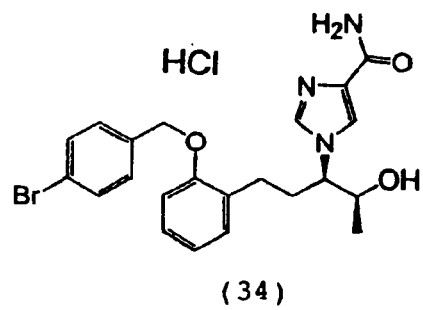
Figure 5:
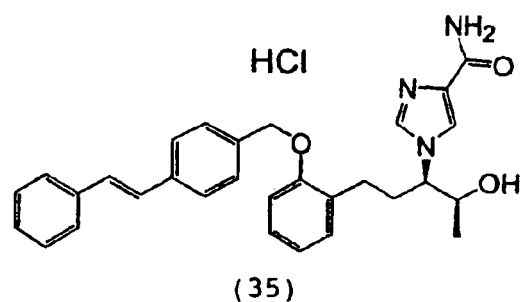
Figure 5:
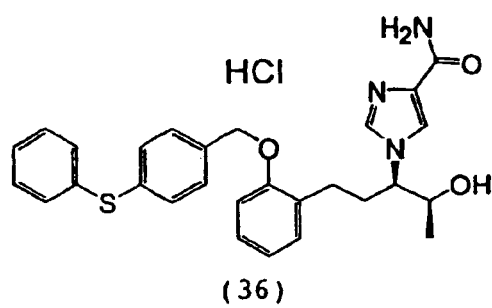
Figure 6:
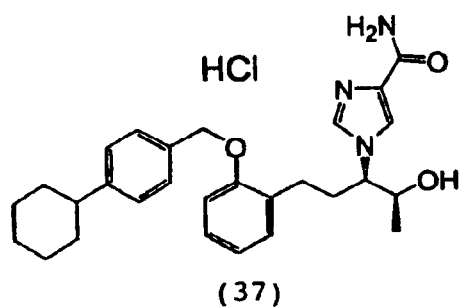
FIG. 6 shows chemical formulae of compound (37) to compound (44).
Figure 6:
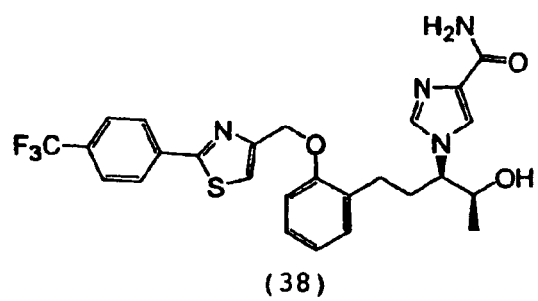
Figure 6:
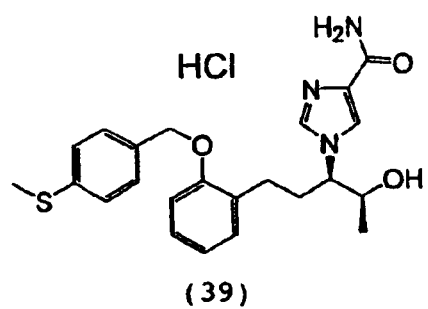
Figure 6:
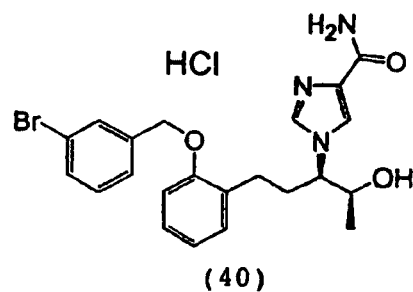
Figure 6:
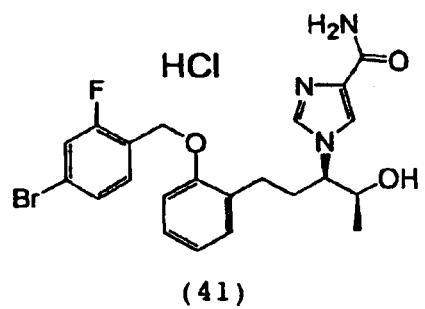
Figure 6:
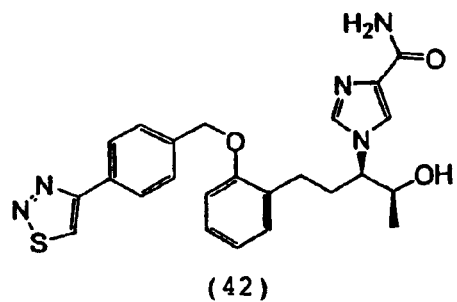
Figure 6:
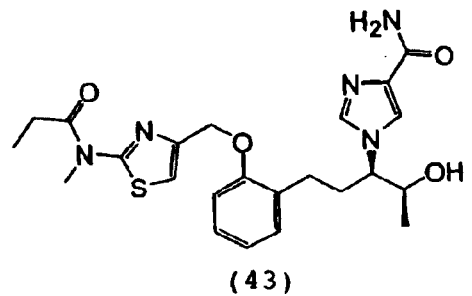
Figure 6:
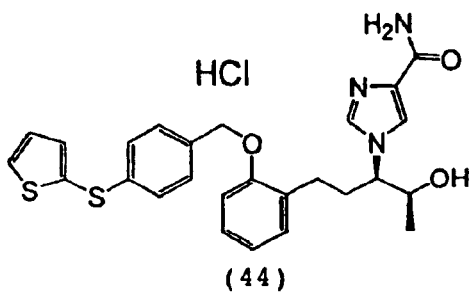
Figure 7:
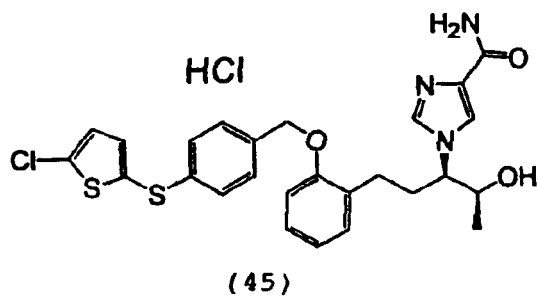
FIG. 7 shows chemical formulae of compound (45) to compound (52).
Figure 7:
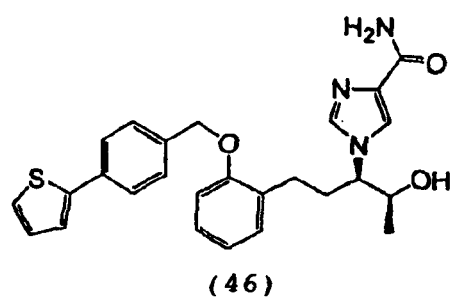
Figure 7:
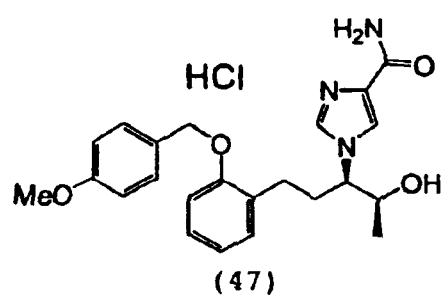
Figure 7:
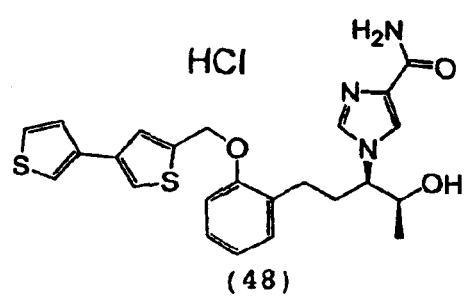
Figure 7:
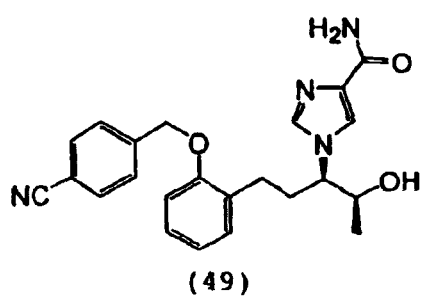
Figure 7:
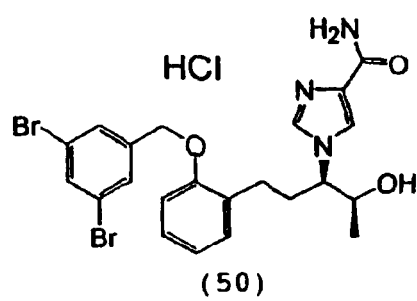
Figure 7:
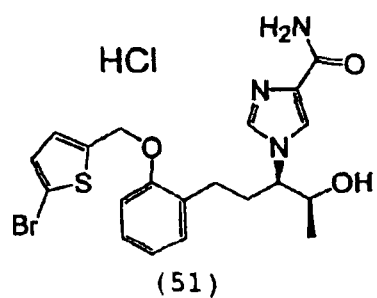
Figure 7:
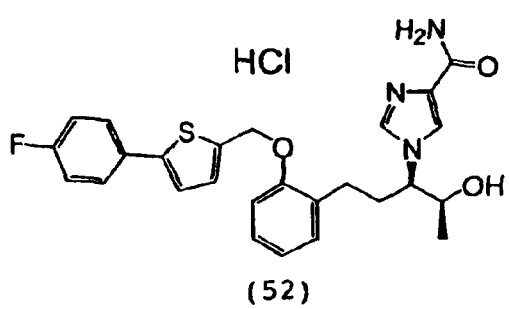
Figure 8:
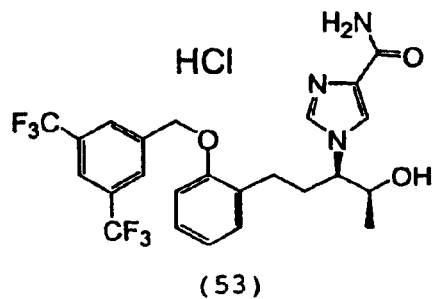
FIG. 8 shows chemical formulae of compound (53) to compound (60).
Figure 8:
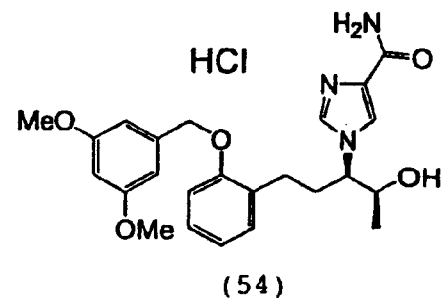
Figure 8:
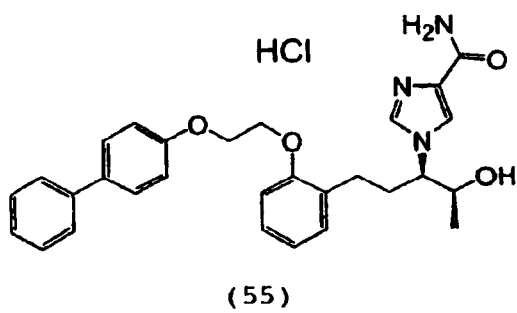
Figure 8:
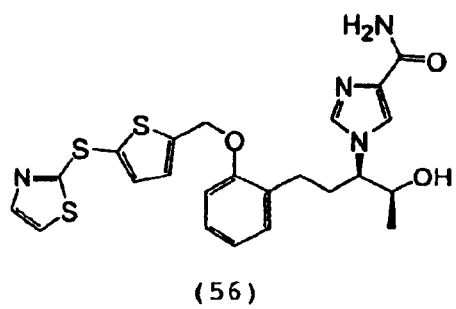
Figure 8:
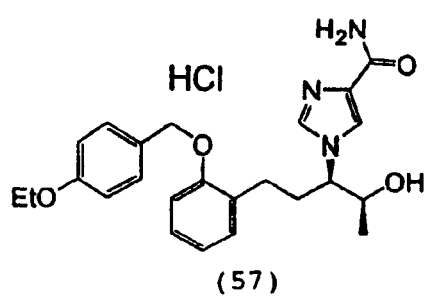
Figure 8:
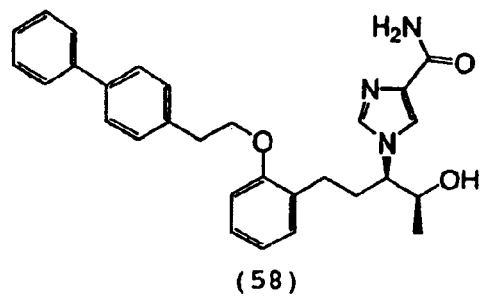
Figure 8:
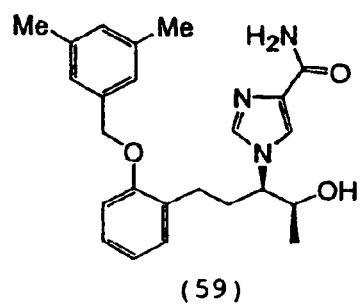
Figure 8:
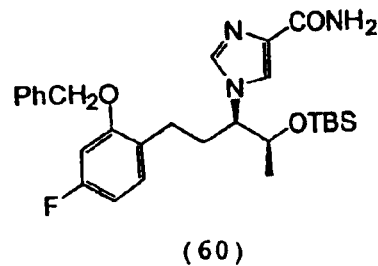
Figure 9:
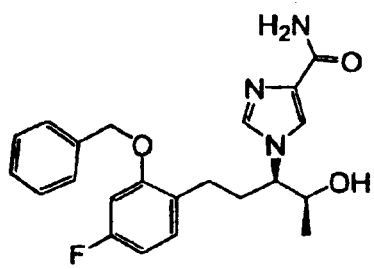
FIG. 9 shows chemical formulae of compound (61) to compound (68).
Figure 9:
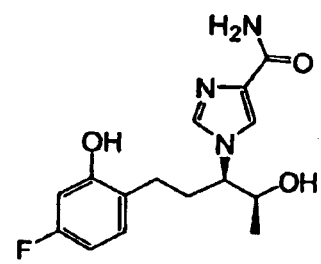
Figure 9:
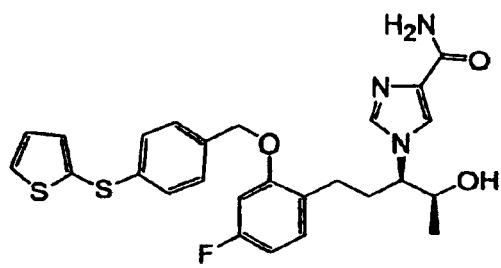
Figure 9:
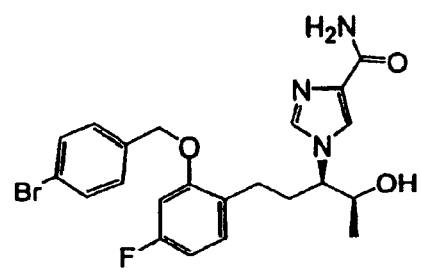
Figure 9:
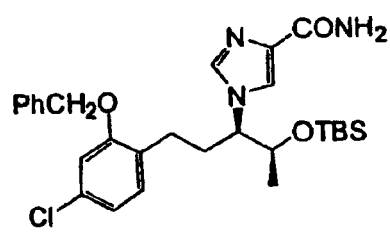
Figure 9:
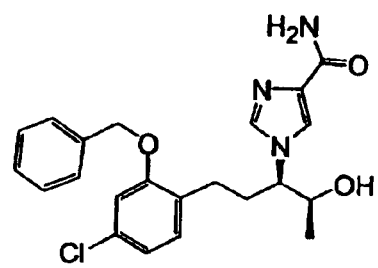
Figure 9:
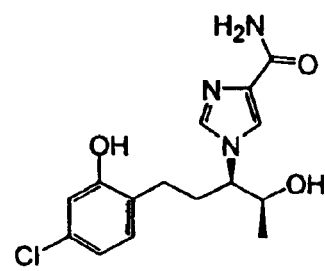
Figure 9:
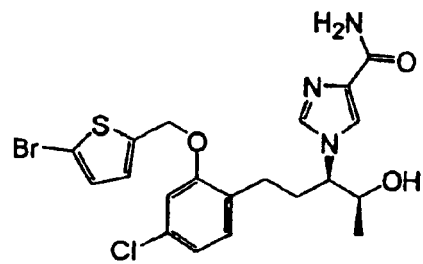
Figure 10:
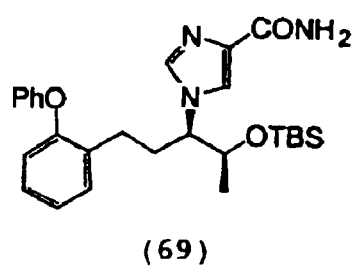
FIG. 10 shows chemical formulae of compound (69) to compound (72).
Figure 10:
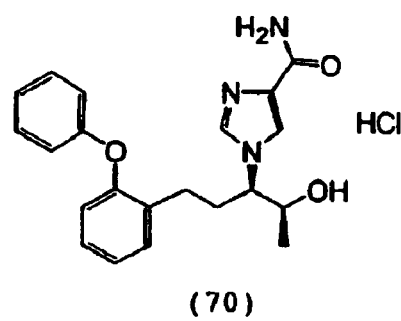
Figure 10:
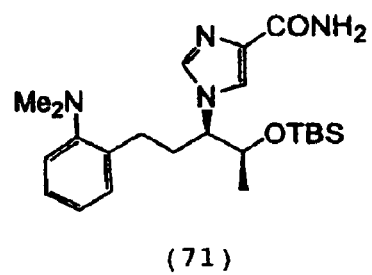
Figure 10:
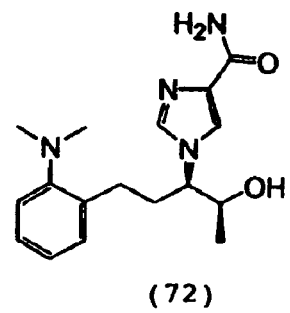

The following Preparation and Examples are given for the purpose of illustrating the present invention in detail, but are not to be construed to limit the scope of the present invention.

Preparation 1

2-Methylthiophenylmethylmagnesium chloride was prepared from magnesium turnings (654 mg) and 2-(chloromethyl)thioanisole (1.55 g) in ether (29 ml) by the method of J. Am. Chem. Soc. (1943) 65, 295. A solution of lithium chloride (38 mg) and copper(II) chloride (60 mg) in THF (2.8 ml) was added dropwise to the ethereal solution of the Grignard reagent followed by addition of a solution of (2RS,3S)-3-(benzyloxy)-1,2-epoxybutane (0.8 g) in ether (8 ml) below −60° C. The mixture was stirred at −70° C. for 1 h, and then allowed to warm to room temperature and stirred overnight. After cooling, the mixture was quenched with saturated aqueous ammonium chloride solution (22 ml). The organic layer was washed with brine, dried over anhydrous magnesium sulfate and concentrated in vacuo to give an oil. Column chromatography ($CH_2Cl_2$) over silica gel gave a pale brown oil of (2S,3S)-2-benzyloxy-5-(2-(methylthio)phenyl)pentan-3-ol (0.65 g, 45.8%).

NMR ($CDCl_3$, δ): 1.20(3H, d, J=6 Hz), 1.6–1.9(2H, m), 2.46(3H, s), 2.66(1H, d, J=3 Hz), 2.7–3.1(2H, m), 3.4–3.6 (2H, m), 4.44(1H, d, J=11 Hz), 4.67(1H, d, J=11 Hz), 7.0–7.4(9H, m).

MS: 339(M+Na)$^+$.

EXAMPLE 1

To an ice-cooled solution of (2S,3S)-2-benzyloxy-5-(2-(methylthio)phenyl)pentan-3-ol (0.64 g) in dichloromethane (12 ml) was added methanesulfonyl chloride (0.234 ml) followed by triethylamine (0.421 ml). The mixture was stirred at 4° C. for 40 min. The mixture was washed with water and brine, dried and concentrated in vacuo to give 2-[(3S,4S)-4-benzyloxy-3-(methanesulfonyloxy)pentyl]-thioanisole (0.92 g) as an oil.

A suspension of imidazole-4-carboxamide (313 mg) in DMF (3.8 ml) was treated with sodium hydride (60% in mineral oil, 129 mg) at ice-bath temperature and the mixture was stirred at room temperature for 20 min. A solution of 2-[(3S,4S)-4-benzyloxy-3-methanesulfonyloxypentyl]thioanisole (0.92 g) in DMF (7.5 ml) was added and the mixture was stirred at 85° C. for 3 days. The mixture was poured into water and extracted with ethyl acetate. The extract was washed with water, dried and concentrated in vacuo. Column chromatography (dichloromethane:methanol=30:1) gave 1-[(2S,3R)-2-benzyloxy-5-(2-(methylthio)phenyl)-3-pentyl]imidazole-4-carboxamide (1) (96.4 mg, 11.6%) as a pale yellow oil.

NMR ($CDCl_3$, d): 1.07(3H, d, J=6 Hz), 2.0–2.4(2H, m), 2.44(3H, s), 2.5–2.7(2H, m), 3.6–3.8(1H, m), 3.9–4.1(1H, m), 4.39(1H, d, J=12 Hz), 4.58(1H, d, J=12 Hz), 5.37 (1H, s), 6.9–7.2 (10H, m), 7.50(1H, d, J=1 Hz), 7.69(1H, d, J=1 Hz).

MS (APCI, m/z): 410(M+H)$^+$.

EXAMPLE 2

A mixture of 1-[(2S,3R)-2-(benzyloxy)-5-(2-(methylthio)phenyl)-3-pentyl]imidazole-4-carboxamide (133 mg) and iodotrimethylsilane (0.16 ml) in chloroform (5 ml) was stirred at room temperature for 2 hours. The mixture was poured into cold methanol and the whole was evaporated in vacuo. The residue was taken up in ethyl acetate, washed with water, aqueous sodium bisulfite and sodium bicarbonate, successively, and dried. The residue left after evaporation of solvent was purified by column chromatography on silica gel, eluting with a mixture of dichloromethane and methanol (20:1) to give a white powder of 1-[(2S,3R)-2-hydroxy-5-(2-(methylthio)phenyl)-3-pentyl]imidazole-4-carboxamide (2) (62 mg).

NMR ($CDCl_3$, δ): 1.11(3H, d, J=6 Hz), 2.0–2.7(5H, m), 2.45(3H, s), 3.9–4.0(2H, m), 5.41(1H, s), 6.9–7.3(5H, m), 7.50(1H, d, J=1 Hz), 7.73(1H, d, J=1 Hz).

MS: 320(M+H)$^+$.

$[\alpha]_D^{22}$=+28.0° (c 1.0, EtOH).

EXAMPLE 3

A mixture of 1-[(2S,3R)-2-hydroxy-5-(2-(methylthio)phenyl)-3-pentyl]imidazole-4-carboxamide (7.1 mg) and m-chloroperbenzoic acid (75%; 5.12 mg) in dichloromethane (1 ml) was stirred at 5° C. for 2 hours. The mixture was purified by column chromatography on silica gel, eluting with a mixture of dichloromethane and methanol (5:1) to give a colorless oil of 1-[(2S,3R)-2-hydroxy-5-(2-(methylsulfinyl)phenyl)-3-pentyl]imidazole-4-carboxamide (3) (5.4 mg).

NMR ($CDCl_3$, δ): 1.0–1.2(3H, m), 2.1–2.9(8H, m), 3.8–4.1(2H, m), 5.50(1H, s), 6.9–7.5(5H, m), 7.7–8.0(2H, m).

MS: 336(M+H)$^+$.

EXAMPLE 4

A mixture of 1-[(2S,3R)-2-hydroxy-5-(2-(methylthio)phenyl)-3-pentyl]imidazole-4-carboxamide (6.0 mg) and m-chloroperbenzoic acid (75%; 13 mg) in dichloromethane (1 ml) was stirred at room temperature overnight. The mixture was purified by column chromatography on silica gel, eluting with a mixture of dichloromethane and methanol (10:1) to give a colorless oil of 1-[(2S,3R)-2-hydroxy-5-(2-(methylsulfonyl)phenyl)-3-pentyl]imidazole-4-carboxamide (4) (4.6 mg).

NMR ($CDCl_3$, δ): 1.13(3H, d, J=6 Hz), 2.0–3.0(5H, m), 3.03(3H, s), 3.9–4.2(2H, m), 5.60(1H, s), 7.08(1H, s), 7.2–8.1(6H, m).

MS: 352(M+H)$^+$.

EXAMPLE 5

A mixture of 1-[(2S,3R)-2-hydroxy-5-(2-hydroxyphenyl)-3-pentyl]imidazole-4-carboxamide (20 mg), 3-(dimethylamino)propyl chloride hydrochloride (32.7 mg) and potassium carbonate (38 mg) in N,N- dimethylformamide (3 ml) was stirred overnight at 60° C. The mixture was evaporated. The residue was purified by column chromatography on silica gel, eluting with a mixture of dichloromethane, triethylamine, and methanol (20:1:4) and the product was treated with HCl in EtOAc to give a pale brown oil of 1-{(2S,3R)-2-hydroxy-5-[2-(3-dimethylaminopropoxy)phenyl]-3-pentyl}imidazole-4-carboxamide dihydrochloride (5) (21.2 mg).

MS: 375(M+H)$^+$.

$[\alpha]_D^{22}$=+2.0° (c 0.50, EtOH).

EXAMPLE 6-1

A mixture of 1-[(2S,3R)-2-hydroxy-5-(2-hydroxyphenyl)-3-pentyl]imidazole-4-carboxamide (0.11 g), 1-bromo-6-phthalimidohexane (0.47 g) and potassium carbonate (0.42 g) in N,N-dimethylformamide (5 ml) was stirred overnight at room temperature. The mixture was taken up in ethyl acetate, washed three times with water, dried, and evaporated. The residue was purified by column chromatography on silica gel, eluting with a mixture of dichloromethane and methanol (20:1) to give a white powder of 1-{(2S,3R)-2-hydroxy-5-[2-(6-phthalimidohexyloxy)phenyl]-3-pentyl}imidazole-4-carboxamide (6-1) (219 mg).

NMR (CDCl$_3$, δ): 1.08(3H, d, J=6 Hz), 1.3–1.9(8H, m), 2.0–2.7(5H, m), 3.6–4.0(6H, m), 5.40(1H, s), 6.7–7.3(5H, m), 7.46(1H, d, J=1 Hz), 7.7–7.9(5H, m).

EXAMPLE 6-2

A mixture of 1-{(2S,3R)-2-hydroxy-5-[2-(6-phthalimidohexyloxy)phenyl]-3-pentyl}imidazole-4-carboxamide (217 mg), hydrazine hydrate (0.04 ml), MeOH (2.9 ml) and tetrahydrofuran (2.9 ml) was stirred overnight at room temperature and evaporated. The residue was purified by column chromatography on silica gel, eluting with a mixture of dichloromethane, acetic acid and methanol (15:1:5) and the product was treated with HCl in EtOAc to give a pale brown powder of 1-{(2S,3R)-2-hydroxy-5-[2-(6-aminohexyloxy)-phenyl]-3-pentyl}imidazole-4-carboxamide dihydrochloride (6-2) (120 mg).

NMR (DMSO-d$_6$, δ): 0.98(3H, d, J=6 Hz), 1.2–1.8(8H, m), 2.0–2.6(4H, m), 2.7–2.9(2H, m), 3.3–4.3(4H, m), 6.7–7.2(4H, m), 7.8–8.4(6H, m), 9.08(1H, s).

MS: 389(M+H)$^+$.

$[\alpha]_D^{23}$=+8.0° (c 0.50, EtOH).

EXAMPLE 7

A mixture of 1-[(2S,3R)-2-hydroxy-5-(2-hydroxyphenyl)-3-pentyl]imidazole-4-carboxamide (10 mg), 2,2,2-trifluoroethyl tosylate (27.4 mg) and potassium carbonate (14.9 mg) in N,N-dimethylformamide (1 ml) was stirred at 130° C. for 13 hours. The mixture was taken up in ethylacetate, washed three times with water, dried, and evaporated. The residue was purified by column chromatography on silica gel, eluting with a mixture of dichloromethane and methanol (10:1) to give a pale brown powder of 1-{(2S,3R)-2-hydroxy-5-[2-(2,2,2-trifluoroethoxy)phenyl]-3-pentyl}imidazole-4-carboxamide (7) (7.0 mg).

NMR (CDCl$_3$, δ): 1.10(3H, d, J=6 Hz), 2.0–2.7(5H, m), 3.8–4.1(2H, m), 4.37(2H, q, J=8 Hz), 5.41(1H, s), 6.78(1H, d, J=8 Hz), 6.9–7.3(4H, m), 7.45(1H, s), 7.68(1H, s).

MS: 372(M+H)$^+$.

$[\alpha]_D^{23}$=+15.6° (c 0.125, EtOH).

EXAMPLE 8

The following compound was prepared by a similar manner to Example 6-1.

1-{(2S,3R)-2-hydroxy-5-[2-(3-(4-chlorophenyl)propoxy)phenyl]-3-pentyl}imidazole-4-carboxamide (8)

NMR (CDCl$_3$, δ): 1.08(3H, d, J=6 Hz), 2.0–2.8(9H, m), 3.8–4.0(4H, m), 5.33(1H, s), 6.7–7.3(9H, m), 7.45(1H, s), 7.70(1H, s).

MS: 442(M+H)$^+$.

$[\alpha]_D^{21}$=+19.4° (c 0.30, EtOH).

Preparation 2

The following compound was prepared by a similar manner to Preparation 1.

(2S,3S)-2-benzyloxy-5-(6-chloro-1-naphthyl)pentan-3-ol

NMR (CDCl$_3$, δ): 1.17(3H, d, J=6 Hz), 1.8–2.0(2H, m), 2.71(1H, d, J=3 Hz), 3.0–3.6(4H, m), 4.42(1H, d, J=11 Hz), 4.67(1H, d, J=11 Hz), 7.3–8.1(11H, m).

MS: 377(M+Na)$^+$.

EXAMPLE 9

The following compound was prepared by a similar manner to Example 1.

1-[(2S,3R)-2-benzyloxy-5-(6-chloro-1-naphthyl)-3-pentyl]-imidazole-4-carboxamide (9)

NMR (CDCl$_3$, d): 1.04(3H, d, J=6 Hz), 2.1–2.6(2H, m), 2.7–3.0(2H, m), 3.6–3.7(1H, m), 3.9–4.0(1H, m), 4.35(1H, d, J=11 Hz), 4.56(1H, d, J=11 Hz), 5.46(1H, s), 6.9–7.9(14H, m).

MS: 448(M+H)$^+$.

EXAMPLE 10

The following compound was prepared by a similar manner to Example 2.

1-[(2S,3R)-2-hydroxy-5-(6-chloro-1-naphthyl)-3-pentyl]imidazole-4-carboxamide (10)

NMR (CDCl$_3$, δ): 1.09(3H, d, J=6 Hz), 2.2–2.5(3H, m), 2.7–3.1(2H, m), 3.8–4.1(2H, m), 5.46(1H, s), 7.01(1H, s), 7.1–7.9(8H, m).

MS: 358(M+H)$^+$.

$[\alpha]_D^{21}$=+15.9° (c 0.50, EtOH).

Preparation 3

The following compound was prepared by a similar manner to Preparation 1.

(2S,3S)-2-benzyloxy-5-(7-chloro-1-naphthyl)pentan-3-ol

NMR (CDCl$_3$, δ): 1.18(3H, d, J=6 Hz), 1.8–2.0(2H, m), 2.69(1H, d, J=4 Hz), 3.0–3.7(4H, m), 4.44(1H, d, J=11 Hz), 4.68(1H, d, J=11 Hz), 7.2–8.1(11H, m).

MS: 377(M+Na)$^+$.

EXAMPLE 11

The following compound was prepared by a similar manner to Example 1.

1-[(2S,3R)-2-benzyloxy-5-(7-chloro-1-naphthyl)-3-pentyl]-imidazole-4-carboxamide (11)

NMR (CDCl$_3$, d): 1.04(3H, d, J=6 Hz), 2.1–2.6(2H, m), 2.7–3.1(2H, m), 3.6–3.7(1H, m), 3.9–4.0(1H, m), 4.36(1H, d, J=11 Hz), 4.56(1H, d, J=11 Hz), 5.40(1H, s), 6.99(1H, s), 7.1–7.9(13H, m).

MS: 448(M+H)$^+$.

EXAMPLE 12

The following compound was prepared by a similar manner to Example 2.

1-[(2S,3R)-2-hydroxy-5-(7-chloro-1-naphthyl)-3-pentyl]imidazole-4-carboxamide (12)

NMR (CDCl$_3$, δ): 1.10(3H, d, J=6 Hz), 2.0–2.6(3H, m), 2.7–3.1(2H, m), 3.9–4.0(2H, m), 5.43(1H, s), 7.01(1H, s), 7.1–7.9(8H, m).

MS: 358(M+H)$^+$.

[α]$_D^{21}$=+38.1° (c 0.10, EtOH).

EXAMPLE 13

To a stirred mixture of 1-naphthol (48.5 mg, 0.336 mmol), 1-[(2S,3R)-2-benzyloxy-5-hydroxy-3-pentyl]imidazole-4-carboxamide (85 mg, 0.280 mmol), and triphenylphosphine (88.2 mg, 0.336 mmol) in tetrahydrofuran (5 ml) was added dropwise diethyl azodicarboxylate (58.6 mg, 0.336 mmol) at ice-bath temperature. After the mixture was stirred overnight at room temperature, the solvent was removed in vacuo. The residue was purified by silica gel (10 g) chromatography eluting with chloroform/methanol (40:1) to give a mixture (60.6 mg) of 1-[(2S,3R)-2-benzyloxy-5-(1-naphthyloxy)-3-pentyl]imidazole-4-carboxamide (13) and by-products. This material was used without further purification.

MS: 430(M+H)$^+$.

EXAMPLE 14

To a solution of 1-[(2S,3R)-2-benzyloxy-5-(1-naphthyloxy)-3-pentyl]imidazole-4-carboxamide (56.5 mg, 0.132 mmol) in cyclohexene (3 ml) and ethanol (6 ml) was added 20% palladium hydroxide on carbon (30 mg). The resulting mixture was stirred at reflux for 22 h.

After cooling to room temperature, the mixture was filtered through Celite and washed with ethanol. The filtrate was concentrated in vacuo and then the residue was purified by silica gel (1.4 g) chromatography eluted with chloroform/methanol (50:1 to 10:1) to give 1-[(2S,3R)-2-hydroxy-5-(1-naphthyloxy)-3-pentyl]imidazole-4-carboxamide (14) (24.8 mg, 55.6%).

IR (KBr, cm$^{-1}$): 3600–2800, 1658, 1589, 1267, 1099

NMR (DMSO-d$_6$, δ): 0.97(3H, d, J=6.2 Hz), 2.30–2.80 (2H, m), 3.70–4.50(4H, m), 5.22(1H, d, J=5.0 Hz), 6.84(1H, d, J=7.3 Hz), 7.03(1H, brs), 7.15–7.60(5H, m), 7.60–8.20 (4H, m).

MS: 340(M+H)$^+$

[α]$_D^{24.2}$=+94.10° (C=0.50, EtOH).

EXAMPLE 15

To a stirred mixture of 1-[(2S,3R)-2-benzyloxy-5-hydroxy-3-pentyl]imidazole-4-carboxamide (85 mg, 0.28 mmol) and methanesulfonyl chloride (64 mg, 0.56 mmol) in dichloromethane (5 ml) was added dropwise triethylamine (57 mg, 0.56 mmol) at ice-bath temperature. After 1 h, the reaction mixture was partitioned between dichloromethane and water. The organic layer was washed with brine, dried (sodium sulfate), and concentrated in vacuo to give 1-[(2S,3R)-2-benzyloxy-5-methylsulfonyoxy-3-pentyl]imidazole-4-carboxamide (106 mg, 99%) as an oil. This material was used immediately without further purification.

Under N$_2$, to a solution of 2-naphthol (49 mg, 0.34 mmol) in DMF (3 ml) was added potassium carbonate (93 mg, 0.67 mmol) at room temperature. The reaction mixture was stirred for 30 minutes. The methanesulfonate prepared above was added and the resulting mixture was stirred for 6 h at 60–70° C. The reaction mixture was poured into water (30 ml) and extracted with ethyl acetate. The organic layer was washed with brine, dried (sodium sulfate) and evaporated in vacuo. The residue was purified by silica gel (4.8 g) chromatography eluting with chloroform/methanol (40:1) to give 1-[(2S,3R)-2-benzyloxy-5-(2-naphthyloxy)-3-pentyl]imidazole-4-carboxamide (15) (51 mg, 42.4%).

IR (KBr, cm$^{-1}$): 3600–2800, 1666, 1595, 1261.

NMR (CDCl$_3$, δ): 1.19(3H, d, J=6.3 Hz), 2.10–2.75(2H, m), 3.60–3.90(2H, m), 4.08(1H, m), 4.30–4.70(3H, m), 5.36(1H, brs), 6.80–7.15(3H, m), 7.20–7.50(8H, m), 7.60–7.80(4H, m).

MS: 430(M+H)$^+$.

[α]$_D^{24.7}$=+59.30° (C=0.50, EtOH).

EXAMPLE 16

This compound was prepared by a similar procedure to that of Example 14.

1-[(2S,3R)-2-hydroxy-5-(2-naphthyloxy)-3-pentyl]imidazole-4-carboxamide (16) (28.6 mg, 79.3%).

IR (KBr, cm$^{-1}$): 3600–2800, 1655, 1597, 1261.

NMR (DMSO-d$_6$, δ): 0.94(3H, d, J=6.2 Hz), 2.20–2.65 (2H, m), 3.65–4.55(4H, m), 5.21(1H, d, J=4.2 Hz), 6.90–7.50(6H, m), 7.60–7.90(5H, m).

MS: 340(M+H)$^+$.

[α]$_D^{24.2}$=+71.20° (C=0.50, EtOH).

EXAMPLE 17

A solution of 1-[(2S,3R)-2-hydroxy-5-(2,3-dichlorophenyl)-3-pentyl]imidazole-4-carboxamide (74 mg) and 4N hydrogen chloride in ethyl acetate (0.2 ml) in methanol (5 ml) was evaporated in vacuo. The residue was crystallized from acetone to give a pale yellow powder of 1-[(2S,3R)-2-hydroxy-5-(2,3-dichlorophenyl)-3-pentyl]imidazole-4-carboxamide hydrochloride (17) (74 mg).

NMR (DMSO-d$_6$, δ): 0.98(3H, d, J=6 Hz), 2.0–2.9(4H, m), 3.8–4.0(1H, m), 4.2–4.4(1H, m), 7.2–7.6(3H, m), 7.79 (1H, s), 8.18(1H, s), 8.30(1H, s), 9.03(1H, s).

MS: 342(M+H)$^+$

EXAMPLE 18

The following compound was prepared by a similar manner to Example 6-1.

1-{(2S,3R)-2-hydroxy-5-[2-(2-(4-chlorophenoxy)ethoxy)phenyl]-3-pentyl}imidazole-4-carboxamide hydrochloride (18)

NMR (DMSO-d$_6$, δ): 0.92(3H, d, J=6 Hz), 2.0–2.5(4H, m), 3.7–3.9(1H, m), 4.1–4.3(1H, m), 4.29(4H, s), 6.8–7.4 (8H, m), 7.73(1H, s), 8.04(1H, s), 8.14(1H, s), 8.82(1H, s).

MS: 444(M+H)$^+$

EXAMPLE 19

The following compound was prepared by a similar manner to Example 6-1.

1-{(2S,3R)-2-hydroxy-5-[2-(2-(4-chlorophenylthio)ethoxy)phenyl]-3-pentyl}imidazole-4-carboxamide (19)

NMR (CDCl$_3$, δ): 1.08(3H, d, J=6 Hz), 1.8–2.7(5H, m), 3.2–3.4(2H, m), 3.8–4.2(4H, m), 5.39(1H, s), 6.7–7.4(9H, m), 7.46(1H, d, J=1 Hz), 7.72(1H, d, J=1 Hz).

MS: 460(M+H)$^+$

EXAMPLE 20

The following compound was prepared by a similar manner to Example 4.

1-{(2S,3R)-2-hydroxy-5-[2-(2-(4-chlorophenylsulfonyl)ethoxy)phenyl]-3-pentyl}imidazole-4-carboxamide (20)

NMR (CDCl$_3$, δ): 1.06(3H, d, J=6 Hz), 1.8–2.7(5H, m), 3.5–4.0(4H, m), 4.2–4.5(2H, m), 5.87(1H, s), 6.7–8.1(11H, m).

MS: 514(M+Na)$^+$

EXAMPLE 21

The following compound was prepared by a similar manner to Example 6-1.

1-{(2S,3R)-2-hydroxy-5-[2-(2-(3,4-dichlorobenzyloxy)ethoxy)phenyl]-3-pentyl}imidazole-4-carboxamide (21)

NMR (CDCl$_3$, δ): 0.96(3H, d, J=6 Hz), 1.97(1H, d, J=5 Hz), 2.1–2.8(4H, m), 3.7–4.2(6H, m), 4.57(1H, d, J=12 Hz), 4.66(1H, d, J=12 Hz), 5.37(1H, s), 6.8–7.5(9H, m), 7.71(1H, s).

MS: 514(M+Na)$^+$

EXAMPLE 22

The following compound was prepared by a similar manner to Example 6-1.

1-{(2S,3R)-2-hydroxy-5-[2-(4-phenylbenzyloxy)phenyl]-3-pentyl}imidazole-4-carboxamide (22)

NMR (CDCl$_3$, δ): 1.03(3H, d, J=6 Hz), 1.75(1H, d, J=5 Hz), 2.0–2.8(4H, m), 3.8–4.0(2H, m), 5.12(2H, s), 5.30(1H, s), 6.8–7.7(16H, m).

MS: 456(M+H)$^+$

EXAMPLE 23

The following compound was prepared by a similar manner to Example 6-1.

1-{(2S,3R)-2-hydroxy-5-[2-(3,4-dichlorobenzyloxy)phenyl]-3-pentyl}imidazole-4-carboxamide (23)

NMR (CDCl$_3$, δ): 1.06(3H, d, J=6 Hz), 2.0–2.7(5H, m), 3.8–4.0(2H, m), 5.01(2H, s), 5.39(1H, s), 6.8–7.5(9H, m), 7.67(1H, s).

MS: 448(M+H)$^+$

EXAMPLE 24

The following compound was prepared by a similar manner to Example 6-1.

1-{(2S,3R)-2-hydroxy-5-[2-(4-phenoxybenzyloxy)phenyl]-3-pentyl}imidazole-4-carboxamide (24)

NMR (CDCl$_3$, δ): 1.03(3H, d, J=6 Hz), 1.81(1H, d, J=5 Hz), 2.0–2.7(4H, m), 3.8–4.0(2H, m), 5.03(2H, s), 5.31(1H, s), 6.8–7.4(15H, m), 7.66(1H, d, J=1 Hz)).

MS: 472(M+H)$^+$

EXAMPLE 25

The following compound was prepared by a similar manner to Example 6-1.

1-{(2S,3R)-2-hydroxy-5-[2-(2-naphthylmethyloxy)phenyl]-3-pentyl}imidazole-4-carboxamide (25)

NMR (CDCl$_3$, δ): 1.00(3H, d, J=6 Hz), 1.8–2.8(5H, m), 3.8–4.0(2H, m), 5.23(2H, s), 5.32(1H, s), 6.8–7.4(9H, m), 7.66(1H, d, J=1 Hz), 7.8–8.0(4H, m).

MS: 430(M+H)$^+$

EXAMPLE 26

The following compound was prepared by a similar manner to Example 6-1.

1-{(2S,3R)-2-hydroxy-5-[2-(4-(1-methyl-1-phenylethyl)benzyloxy)phenyl]-3-pentyl}imidazole-4-carboxamide (26)

NMR (CDCl$_3$, δ): 1.00(3H, d, J=6 Hz), 1.70(6H, s), 1.81(1H, d, J=5 Hz), 2.0–2.7(4H, m), 3.8–4.0(2H, m), 5.03(2H, s), 5.33(1H, s), 6.8–7.4(15H, m), 7.65(1H, d, J=1 Hz).

MS: 498(M+H)$^+$

EXAMPLE 27

The following compound was prepared by a similar manner to Example 6-1.

1-{(2S,3R)-2-hydroxy-5-[2-(4-(2-pyridyl)benzyloxy)phenyl]-3-pentyl}imidazole-4-carboxamide (27)

NMR (CDCl$_3$, δ): 1.02(3H, d, J=6 Hz), 2.0–2.7(5H, m), 3.8–4.0(2H, m), 5.13(2H, s), 5.39(1H, s), 6.8–8.1(14H, m), 8.69(1H, d, J=5 Hz).

MS: 457(M+H)$^+$

EXAMPLE 28

The following compound was prepared by a similar manner to Example 6-1.

1-{(2S,3R)-2-hydroxy-5-[2-(4-(4-fluorophenoxy)benzyloxy)phenyl]-3-pentyl}imidazole-4-carboxamide (28)

NMR (CDCl$_3$, δ): 1.03(3H, d, J=6 Hz), 1.8–2.7(5H, m), 3.8–4.0(2H, m), 5.02(2H, s), 5.33(1H, s), 6.8–7.7(15H, m).

MS: 490(M+H)$^+$

EXAMPLE 29

The following compound was prepared by a similar manner to Example 6-1.

1-{(2S,3R)-2-hydroxy-5-[2-(3-(phenoxymethyl)benzyloxy)phenyl]-3-pentyl}imidazole-4-carboxamide (29)

NMR (CDCl$_3$, δ): 0.98(3H, d, J=6 Hz), 1.95(1H, d, J=5 Hz), 2.0–2.7(4H, m), 3.8–3.9(2H, m), 5.09(2H, s), 5.10(2H, s), 5.35(1H, s), 6.8–7.7(16H, m).

MS: 486(M+H)$^+$

EXAMPLE 30

The following compound was prepared by a similar manner to Example 6-1.

1-{(2S,3R)-2-hydroxy-5-[2-(4-isopropylbenzyloxy)phenyl]-3-pentyl}imidazole-4-carboxamide (30)

NMR (CDCl$_3$, δ): 1.01(3H, d, J=6 Hz), 1.26(6H, d, J=7 Hz), 1.93(1H, d, J=5 Hz), 2.0–2.7(4H, m) 2.8–3.0(1H, m), 3.8–4.0(2H, m), 5.04(2H, s), 5.37(1H, s), 6.8–7.4(10H, m), 7.66(1H, d, J=1 Hz).

MS: 422(M+H)$^+$

EXAMPLE 31

The following compound was prepared by a similar manner to Example 6-1.

1-{(2S,3R)-2-hydroxy-5-[2-(4-(2-cyano-1-pyrrolyl)-3-fluorobenzyloxy)phenyl]-3-pentyl}imidazole-4-carboxamide (31)

NMR (CDCl$_3$, δ): 1.05(3H, d, J=6 Hz), 2.0–2.7(5H, m), 3.8–4.0(2H, m), 5.10(2H, s), 5.36(1H, s), 6.3–6.5(1H, m), 6.8–7.6(11H, m), 7.65(1H, d, J=1 Hz).

MS: 488(M+H)$^+$

EXAMPLE 32

The following compound was prepared by a similar manner to Example 6-1.

1-{(2S,3R)-2-hydroxy-5-[2-(5-(4-tert-butylphenyl)-1,2,4-oxadiazol-3-ylmethyloxy)phenyl]-3-pentyl}imidazole-4-carboxamide (32)

NMR (CDCl$_3$, δ): 1.09(3H, d, J=6 Hz), 1.36(9H, s), 2.1–2.8(5H, m), 3.9–4.1(2H, m), 5.35(1H, s), 5.39(2H, s), 6.8–7.6(8H, m), 7.72(1H, d, J=1 Hz), 8.01(2H, d, J=8 Hz).

MS: 504(M+H)$^+$

EXAMPLE 33

The following compound was prepared by a similar manner to Example 6-1.

1-{(2S,3R)-2-hydroxy-5-[2-(4-chlorobenzyloxy)phenyl]-3-pentyl}imidazole-4-carboxamide hydrochloride (33)

NMR (DMSO-d$_6$, δ): 0.94(3H, d, J=6 Hz), 2.0–2.6(4H, m), 3.8–3.9(1H, m), 4.1–4.3(1H, m), 5.09(2H, s), 6.8–7.5 (8H, m), 7.79(1H, s), 8.14(1H, s), 8.23(1H, s), 8.96(1H, s).

MS: 414(M+H)$^+$

EXAMPLE 34

The following compound was prepared by a similar manner to Example 6-1.

1-{(2S,3R)-2-hydroxy-5-[2-(4-bromobenzyloxy)phenyl]-3-pentyl}imidazole-4-carboxamide hydrochloride (34)

NMR (DMSO-d$_6$, δ): 0.94(3H, d, J=6 Hz), 2.0–2.6(4H, m), 3.8–3.9(1H, m), 4.1–4.3(1H, m), 5.08(2H, s), 6.8–7.3 (4H, m), 7.34(2H, d, J=8 Hz), 7.58(2H, d, J=8 Hz), 7.70(1H, s), 8.00(1H, s), 8.15(1H, s), 8.82(1H, s).

MS: 458, 460

EXAMPLE 35

The following compound was prepared by a similar manner to Example 6-1.

1-{(2S,3R)-2-hydroxy-5-[2-(4-(E)-styrylbenzyloxy)phenyl]-3-pentyl}imidazole-4-carboxamide hydrochloride (35)

NMR (DMSO-d$_6$, δ): 0.96(3H, d, J=6 Hz), 2.0–2.7(4H, m), 3.8–3.9(1H, m), 4.1–4.3(1H, m), 5.11(2H, s), 6.8–7.7 (15H, m), 7.77(1H, s), 8.10(1H, s), 8.21(1H, s), 8.91(1H, s).

MS: 482(M+H)$^+$

EXAMPLE 36

The following compound was prepared by a similar manner to Example 6-1.

1-{(2S,3R)-2-hydroxy-5-[2-(4-(phenylthio)benzyloxy)phenyl]-3-pentyl}imidazole-4-carboxamide hydrochloride (36)

NMR (DMSO-d$_6$, δ): 0.93(3H, d, J=6 Hz), 2.0–2.7(4H, m), 3.8–3.9(1H, m), 4.1–4.3(1H, m), 5.10(2H, s), 6.8–7.5 (13H, m), 7.75(1H, s), 8.09(1H, s), 8.20(1H, s), 8.91(1H, s).

MS: 488(M+H)$^+$

EXAMPLE 37

The following compound was prepared by a similar manner to Example 6-1.

1-{(2S,3R)-2-hydroxy-5-[2-(4-cyclohexylbenzyloxy)phenyl]-3-pentyl}imidazole-4-carboxamide hydrochloride (37)

NMR (DMSO-d$_6$, δ): 0.93(3H, d, J=6 Hz) 1.1–1.9(10H, m), 2.0–2.6(5H, m), 3.8–3.9(1H, m), 4.1–4.3(1H, m), 5.05 (2H, s), 6.8–7.4(8H, m), 7.72(1H, s), 8.04(1H, s), 8.17(1H, s), 8.84(1H, s).

MS: 462(M+H)$^+$

EXAMPLE 38

The following compound was prepared by a similar manner to Example 6-1.

1-{(2S,3R)-2-hydroxy-5-[2-(2-(4-(trifluoromethyl)phenyl)-4-thiazolylmethyloxy)phenyl]-3-pentyl}imidazole-4-carboxamide (38)

NMR (CDCl$_3$, δ): 1.02(3H, d, J=6 Hz), 2.17(1H, d, J=5 Hz), 2.3–2.8(4H, m), 3.8–4.0(2H, m), 5.26(2H, s), 5.36(1H, s), 6.9–7.5(7H, m), 7.6–7.8(3H, m), 8.08(2H, d, J=8 Hz).

MS: 531(M+H)$^+$

EXAMPLE 39

The following compound was prepared by a similar manner to Example 6-1.

1-{(2S,3R)-2-hydroxy-5-[2-(4-(methylthio)benzyloxy)phenyl]-3-pentyl}imidazole-4-carboxamide hydrochloride (39)

NMR (DMSO-d$_6$, δ): 0.95(3H, d, J=6 Hz), 2.0–2.6(4H, m), 3.8–3.9(1H, m), 4.1–4.3(1H, m), 5.05(2H, s), 6.8–7.4 (8H, m), 7.80(1H, s), 8.15(1H, s), 8.24(1H, s), 8.97(1H, s).

MS: 426(M+H)$^+$

EXAMPLE 40

The following compound was prepared by a similar manner to Example 6-1.

1-{(2S,3R)-2-hydroxy-5-[2-(3-bromobenzyloxy)phenyl]-3-pentyl}imidazole-4-carboxamide hydrochloride (40)

NMR (DMSO-d$_6$, δ): 0.95(3H, d, J=6 Hz), 2.0–2.7(4H, m), 3.8–4.0(1H, m), 4.1–4.3(1H, m), 5.12(2H, s), 6.8–7.7 (8H, m), 7.74(1H, s), 8.08(1H, s), 8.20(1H, s), 8.93(1H, s).

MS: 458, 460

EXAMPLE 41

The following compound was prepared by a similar manner to Example 6-1.

1-{(2S,3R)-2-hydroxy-5-[2-(4-bromo-2-fluorobenzyloxy)phenyl]-3-pentyl}imidazole-4-carboxamide hydrochloride (41)

NMR (DMSO-d$_6$, δ): 0.93(3H, d, J=6 Hz), 2.0–2.6(4H, m), 3.8–3.9(1H, m), 4.1–4.3(1H, m), 5.11(2H, s), 6.8–7.7 (7H, m), 7.77(1H, s), 8.10(1H, s), 8.19(1H, s), 8.92(1H, s).

MS: 476, 478

EXAMPLE 42

The following compound was prepared by a similar manner to Example 6-1.

1-{(2S,3R)-2-hydroxy-5-[2-(4-(1,2,3-thiadiazol-4-yl)benzyloxy)phenyl]-3-pentyl}imidazole-4-carboxamide (42)

NMR (CDCl$_3$, δ): 1.05(3H, d, J=6 Hz), 1.9–2.8(5H, m), 3.8–4.0(2H, m), 5.13(2H, s), 5.36(1H, s), 6.8–7.5(6H, m), 7.51(2H, d, J=8 Hz), 7.67(1H, d, J=1 Hz), 8.10(2H, d, J=8 Hz), 8.76(1H, s).

MS: 464(M+H)$^+$

EXAMPLE 43

The following compound was prepared by a similar manner to Example 6-1.

1-{(2S,3R)-2-hydroxy-5-[2-(2-(N-methylpropionylamino)-4-thiazolylmethyloxy)phenyl]-3-pentyl}imidazole-4-carboxamide (43)

NMR (CDCl$_3$, δ): 1.03(3H, d, J=6 Hz), 1.28(3H, t, J=7 Hz), 2.0–2.8(7H, m), 3.70(3H, s), 3.8–4.0(2H, m), 5.09(2H, s), 5.37(1H, s), 6.8–7.3(6H, m), 7.42(1H, d, J=1 Hz), 7.67 (1H, d, J=1 Hz).

MS: 472(M+H)$^+$

EXAMPLE 44

The following compound was prepared by a similar manner to Example 6-1.

1-{(2S,3R)-2-hydroxy-5-[2-(4-(2-thienylthio)benzyloxy)phenyl]-3-pentyl}imidazole-4-carboxamide hydrochloride (44)

NMR (DMSO-$d_6$, δ): 0.92(3H, d, J=6 Hz), 2.0–2.6(4H, m), 3.8–3.9(1H, m), 4.1–4.3(1H, m), 5.05(2H, s), 6.8–7.5 (10H, m), 7.72(1H, s), 7.83(1H, dd, J=5,1 Hz), 8.05(1H, s), 8.17(1H, s), 8.84(1H, s).

MS: 494(M+H)$^+$

EXAMPLE 45

The following compound was prepared by a similar manner to Example 6-1.

1-{(2S,3R)-2-hydroxy-5-[2-(4-(5-chloro-2-thienylthio)benzyloxy)phenyl]-3-pentyl}imidazole-4-carboxamide hydrochloride (45)

NMR (DMSO-$d_6$, δ): 0.92(3H, d, J=6 Hz), 2.0–2.6(4H, m), 3.8–3.9(1H, m), 4.1–4.3(1H, m), 5.07(2H, s), 6.8–7.5 (10H, m), 7.74(1H, s), 8.08(1H, s), 8.19(1H, s), 8.89(1H, s).

MS: 528(M+H)$^+$

EXAMPLE 46

The following compound was prepared by a similar manner to Example 6-1.

1-{(2S,3R)-2-hydroxy-5-[2-(4-(2-thienyl)benzyloxy)phenyl]-3-pentyl}imidazole-4-carboxamide (46)

NMR (CDCl$_3$, δ): 1.03(3H, d, J=6 Hz), 1.7–2.8(5H, m), 3.8–4.0(2H, m), 5.07(2H, s), 5.34(1H, s), 6.8–7.7(14H, m).

MS: 462(M+H)$^+$

EXAMPLE 47

The following compound was prepared by a similar manner to Example 6-1.

1-{1(2S,3R)-2-hydroxy-5-[2-(4-methoxybenzyloxy)phenyl]-3-pentyl}imidazole-4-carboxamide hydrochloride (47)

NMR (DMSO-$d_6$, δ): 0.94(3H, d, J=6 Hz), 2.0–2.6(4H, m), 3.76(3H, s), 3.8–3.9(1H, m), 4.1–4.3(1H, m), 5.00(2H, s), 6.8–7.4(8H, m), 7.79(1H, s), 8.14(1H, s), 8.22(1H, s), 8.94(1H, s).

MS: 410(M+H)$^+$

EXAMPLE 48

The following compound was prepared by a similar manner to Example 6-1.

1-{(2S,3R)-2-hydroxy-5-[2-(4-(3-thienyl)-2-thienylmethyloxy)phenyl]-3-pentyl}imidazole-4-carboxamide hydrochloride (48)

NMR (DMSO-$d_6$, δ): 0.94(3H, d, J=6 Hz), 2.0–2.6(4H, m), 3.8–3.9(1H, m), 4.1–4.3(1H, m), 5.30(2H, s), 6.8–7.8 (10H, m), 7.95(1H, s), 8.09(1H, s), 8.72(1H, s).

MS: 468(M+H)$^+$

EXAMPLE 49

The following compound was prepared by a similar manner to Example 6-1.

1-{(2S,3R)-2-hydroxy-5-[2-(4-cyanobenzyloxy)phenyl]-3-pentyl}imidazole-4-carboxamide (49)

NMR (DMSO-$d_6$, δ): 0.87(3H, d, J=6 Hz) 2.0–2.5(4H, m), 3.7–4.0(2H, m), 5.08(1H, d, J=5 Hz) 5.20(2H, s), 6.8–7.4(6H, m), 7.55(2H, d, J=8 Hz), 7.70(1H, s), 7.73(1H, s), 7.87(2H, d, J=8 Hz).

MS: 405(M+H)$^+$

EXAMPLE 50

The following compound was prepared by a similar manner to Example 6-1.

1-{(2S,3R)-2-hydroxy-5-[2-(3,5-dibromobenzyloxy)phenyl]-3-pentyl}imidazole-4-carboxamide hydrochloride (50)

NMR (DMSO-$d_6$, δ): 0.96(3H, d, J=6 Hz), 2.0–2.7(4H, m), 3.8–3.9(1H, m), 4.1–4.3(1H, m), 5.14(2H, s), 6.8–7.3 (4H, m), 7.63(2H, d, J=2 Hz), 7.73(1H, s), 7.80(1H, d, J=2 Hz), 8.07(1H, s), 8.20(1H, s), 8.91(1H, s).

MS: 536, 538, 540

EXAMPLE 51

The following compound was prepared by a similar manner to Example 6-1.

1-{(2S,3R)-2-hydroxy-5-[2-(5-bromo-2-thienylmethyloxy)phenyl]-3-pentyl}imidazole-4-carboxamide hydrochloride (51)

NMR (DMSO-$d_6$, δ): 0.95(3H, d, J=6 Hz), 2.0–2.6(4H, m), 3.8–3.9(1H, m), 4.1–4.3(1H, m), 5.26(2H, s), 6.8–7.3 (6H, m), 7.78(1H, s), 8.15(1H, s), 8.24(1H, s), 8.96(1H, s).

MS: 464, 466

EXAMPLE 52

The following compound was prepared by a similar manner to Example 6-1.

1-{(2S,3R)-2-hydroxy-5-[2-(5-(4-fluorophenyl)-2-thienylmethyloxy)phenyl]-3-pentyl}imidazole-4-carboxamide hydrochloride (52)

NMR (DMSO-$d_6$, δ): 0.95(3H, d, J=6 Hz), 2.0–2.6(4H, m), 3.8–3.9(1H, m), 4.1–4.3(1H, m), 5.30(2H, s), 6.7–7.8 (11H, m), 8.04(1H, s), 8.17(1H, s), 8.85(1H, s).

MS: 480(M+H)$^+$

EXAMPLE 53

The following compound was prepared by a similar manner to Example 6-1.

1-{(2S,3R)-2-hydroxy-5-[2-(3,5-bis(trifluoromethyl)benzyloxy)phenyl]-3-pentyl}imidazole-4-carboxamide hydrochloride (53)

NMR (DMSO-$d_6$, δ): 0.90(3H, d, J=6 Hz), 2.0–2.7(4H, m), 3.8–3.9(1H, m), 4.1–4.3(1H, m), 5.33(2H, s), 6.8–7.3 (4H, m), 7.66(1H, s), 7.95(1H, s), 8.12(4H, s), 8.81(1H, s).

MS: 516(M+H)$^+$

EXAMPLE 54

The following compound was prepared by a similar manner to Example 6-1.

1-{(2S,3R)-2-hydroxy-5-[2-(3,5-dimethoxybenzyloxy)phenyl]-3-pentyl}imidazole-4-carboxamide hydrochloride (54)

NMR (DMSO-$d_6$, δ): 0.94(3H, d, J=6 Hz), 2.0–2.7(4H, m), 3.73(6H, s), 3.8–3.9(1H, m), 4.1–4.3(1H, m), 5.05(2H, s), 6.4–6.6(3H, s), 6.8–7.2(4H, m), 7.72(1H, s), 8.05(1H, s), 8.18(1H, s), 8.88(1H, s).

MS: 440(M+H)$^+$

EXAMPLE 55

The following compound was prepared by a similar manner to Example 6-1.

1-{(2S,3R)-2-hydroxy-5-[2-(2-(4-biphenylyloxy)ethyloxy)phenyl]-3-pentyl}imidazole-4-carboxamide hydrochloride (55)

NMR (DMSO-$d_6$, δ): 0.92(3H, d, J=6 Hz), 2.0–2.6(4H, m), 3.7–3.9(1H, m), 4.0–4.2(1H, m), 4.34(4H, s), 6.8–7.7 (14H, m), 7.95(1H, s), 8.09(1H, s), 8.71(1H, s).

MS: 486(M+H)$^+$

EXAMPLE 56

The following compound was prepared by a similar manner to Example 6-1.

1-{(2S,3R)-2-hydroxy-5-[2-(5-(2-thiazolylthio)-2-thienylmethyloxy)phenyl]-3-pentyl}imidazole-4-carboxamide (56)

NMR (CDCl$_3$, δ): 1.04(3H, d, J=6 Hz), 2.0–2.7(5H, m), 3.8–4.1(2H, m), 5.23(2H, s), 5.39(1H, s), 6.8–7.7(11H, m).

MS: 501(M+H)$^+$

EXAMPLE 57

The following compound was prepared by a similar manner to Example 6-1.

1-{(2S,3R)-2-hydroxy-5-[2-(4-ethoxybenzyloxy)phenyl]-3-pentyl}imidazole-4-carboxamide hydrochloride (57)

NMR (DMSO-d$_6$, δ): 0.94(3H, d, J=6 Hz), 1.33(3H, t, J=7 Hz), 2.0–2.6(4H, m), 3.8–3.9(1H, m), 4.02(2H, q, J=7 Hz), 4.1–4.3(1H, m), 5.00(2H, s), 6.7–7.4(8H, m), 7.75(1H, s), 8.09(1H, s), 8.19(1H, s), 8.87(1H, s).

MS: 424(M+H)$^+$

EXAMPLE 58

The following compound was prepared by a similar manner to Example 6-1.

1-{(2S,3R)-2-hydroxy-5-[2-(2-(4-biphenylyl)ethyloxy)phenyl]-3-pentyl}imidazole-4-carboxamide (58)

NMR (CDCl$_3$, δ): 0.95(3H, d, J=6 Hz), 1.6–2.7(5H, m), 3.15(2H, t, J=7 Hz), 3.7–3.9(2H, m), 4.24(2H, t, J=7 Hz), 5.35(1H, s), 6.8–7.7(16H, m).

MS: 470(M+H)$^+$

EXAMPLE 59

The following compound was prepared by a similar manner to Example 6-1.

1-{(2S,3R)-2-hydroxy-5-[2-(3,5-dimethylbenzyloxy)phenyl]-3-pentyl}imidazole-4-carboxamide (59)

NMR (CDCl$_3$, δ): 1.03(3H, d, J=6 Hz), 1.83(1H, d, J=5 Hz), 2.0–2.7(4H, m), 2.34(6H, s), 3.8–4.0(2H, m), 5.00(2H, s), 5.35(1H, s), 6.8–7.2(8H, m), 7.37(1H, d, J=1 Hz), 7.66 (1H, d, J=1 Hz).

MS: 408(M+H)$^+$

Preparation 4

A mixture of 4-fluorosalicylic acid (5.16 g), benzyl bromide (8.68 ml) and potassium carbonate (10 g) in N,N-dimethylformamide (DMF; 30 ml) was stirred at room temperature for 5 hr.

The mixture was diluted with EtOAc and washed with water twice. The orgnic extract was dried and evaporated to give an oil (12.5 g), which was chromatographed over silica gel (70 g) eluting with a mixture of hexane and EtOAc (50:1 to 10:1) to give colorless crystals of benzyl 2-(benzyloxy)-4-fluorobenzoate (10.3 g, 93.0%).

NMR (CDCl$_3$, δ): 5.14(2H, s), 5.33(2H, s), 6.6–6.8(2H, m), 7.3–7.5(10H, m), 7.8–8.0(1H, m).

MS: 359(M+Na)$^+$

Preparation 5

THF (45 ml) and benzyl 2-(benzyloxy)-4-fluorobenzoate (10.3 g) were added portionwise to a mixture of lithium aluminium hydride (1.16 g) and diethyl ether (45 ml) below 20° C. under nitrogen atmosphere. The mixture was stirred at room temperature for 4 hr.

Aqueous sulfuric acid (10%; 13.6 ml) was added dropwise. The mixture was filtered through Celite and washed with ether.

The filtrate was dried and evaporated. Benzyl alcohol produced was removed in vacuo (bath temp. 110° C.). The residue (10.8 g) was chromatographed over silica gel (100 g) eluting with a mixture of hexane and dichloromethane (5:1) to dichloromethane to give a colorless oil of 2-(benzyloxy)-4-fluorobenzyl alcohol (6.5 g, 91.9%).

NMR (CDCl$_3$, δ): 2.14(1H, t, J=7 Hz), 4.69(2H, d, J=7 Hz), 5.09(2H, s), 6.6–6.8(2H, m), 7.2–7.5(6H, m).

MS: 255(M+Na)$^+$

Preparation 6

A mixture of 2-(benzyloxy)-4-fluorobenzyl alcohol (6.54 g) and manganese(IV) oxide (9.04 g) in chloroform (70 ml) was refluxed and stirred for 2 hr. The insoluble material was removed by filtration and washed with chloroform. The filrate was evaporated and the residue (6.7 g) was chromatographed over silica gel (90 g) eluting with a mixture of hexane and dichloromethane (5:1) to dichloromethane to give a colorless oil of 2-(benzyloxy)-4-fluorobenzaldehyde (3.8 g, 59%).

NMR (CDCl$_3$, δ): 5.17(2H, s), 6.7–6.8(2H, m), 7.3–7.5 (5H, m), 7.8–8.0(1H, m), 10.44(1H, s).

Preparation 7

A solution of butyl lithium in hexane (1.6 M; 8.18 ml) was added dropwise below –50° C. to a solution of dimethyl (3S)-tert-butyldimethylsilyloxy-2-oxo-1-butylphosphonate (4.06 g) in THF (23 ml). The mixture was stirred for 10 min.

A solution of 2-benzyloxy-4-fluorobenzaldehyde (3.61 g) in THF (19 ml) was added dropwise to the above mixture and the temperature was allowed to rise gradually to 0° C. and kept overnight, then at room temperature for 1 day.

Aqueous saturated sodium bicarbonate (60 ml) and dichloromethane (60 ml) were added. The organic layer was washed with water, dried and evaporated. The residue (6.3 g) was chlomatographed over silica gel (120 g) eluting with a mixture of hexane and EtOAc (40:1) to give a yellow oil of (S)-1-(2-benzyloxy-4-fluorophenyl)-4-tert-butyldimethylsilyloxy-1-penten-3-one (63) (3.95 g, 72.9%).

NMR (CDCl$_3$, δ): 0.06(3H, s), 0.07(3H, s), 0.91(9H, s), 1.33(3H, d, J=7 Hz), 4.31(1H, q, J=7 Hz), 5.15(2H, s), 6.6–6.8(2H, m), 7.2–7.6(7H, m), 8.03(1H, d, J=16 Hz).

MS: 415(M+H)$^+$

Preparation 8

1M solution of L-selectride in THF (11.5 ml) was added dropwise below –30° C. to a solution of (S)-1-(2-benzyloxy-4-fluorophenyl)-4-tert-butyldimethylsilyloxy-1-penten-3-one (3.94 g) in THF (18 ml). The mixture was stirred at –20° C. for 30 min. Water and EtOAc were added and the organic layer was washed with brine, dried and evaporated. The residue was chromatographed over silica gel (100 g) eluting with a mixture of hexane and EtOAc (30:1) to afford a pale yellow oil of (3S,4S)-1-(2-benzyloxy-4-fluorophenyl)-4-tert-butyldimethylsilyloxy-1-penten-3-ol (2.64 g, 66.7%).

NMR (CDCl$_3$, δ): 0.08(3H, s), 0.09(3H, s), 0.90(9H, s), 1.17(3H, d, J=6 Hz), 2.67(1H, d, J=4 Hz), 3.6–4.0(2H, m), 5.08(2H, s), 6.0–6.2(1H, m), 6.6–7.0(3H, m), 7.3–7.5(6H, m).

MS: 439(M+Na)$^+$

Preparation 9

A mixture of (3S,4S)-1-(2-benzyloxy-4-fluorophenyl)-4-tert-butyldimethylsilyloxy-1-penten-3-ol (2.62 g) and 10% Pd—C (0.52 g) in EtOAc (65 ml) was stirred under hydrogen atmosphere at atmospheric pressure for 13 min. Pd—C was removed by filtration and the filtrate was evaporated. The residual oil (2.38 g) was chromatographed over silica gel (30 g) eluting with a mixture of hexane and EtOAc (50:1 to 2:1) to give a colorless oil of (3S,4S)-1-(2-benzyloxy-4-fluorophenyl)-4-tert-butyldimethylsilyloxy-3-pentanol (1.35 g, 51.3%) and (3S,4S)-1-(2-hydroxy-4-fluorophenyl)-4-tert-butyldimethylsilyloxy-3-pentanol (0.94 g, 45.5%).

(3S,4S)-1-(2-hydroxy-4-fluorophenyl)-4-tert-butyldimethylsilyloxy-3-pentanol (0.94 g) was treated with benzyl bromide (0.48 ml) and potassium carbonate (0.53 g) in DMF (5 ml) at room temperature for 2 hr. The mixture was diluted with EtOAc and washed with water twice, dried and evaporated. The residual oil (1.43 g) was chromatographed over silica gel (30 g), eluting with a mixture of hexane and EtOAc (40:1) to give a second crop of colorless oil of (3S,4S)-1-(2-benzyloxy-4-fluorophenyl)-4-tert-butyldimethylsilyloxy-3-pentanol (0.79 g, total yield 81.4%).

NMR (CDCl$_3$, δ): 0.05(3H, s), 0.06(3H, s), 0.88(9H, s), 1.07(3H, d, J=6 Hz), 1.5–1.8(2H, m), 2.38(1H, d, J=5 Hz), 2.6–3.0(2H, m), 3.2–3.4(1H, m), 3.5–3.7(1H, m), 5.05(2H, s), 6.5–6.7(2H, m), 7.0–7.5(6H, m).

MS: 441(M+Na)$^+$

Preparation 10

A solution of triethylamine (1.05 ml) in dichloromethane (3 ml) was added dropwise to an ice-cooled solution of (3S,4S)-1-(2-benzyloxy-4-fluorophenyl)-4-tert-butyldimethylsilyloxy-3-pentanol (2.13 g) and methanesulfonyl chloride (0.588 ml) in dichloromethane (42 ml) and the mixture was stirred at 5° C. for 30 min. The mixture was washed with water, dried and evaporated.

The residual oil (2.80 g) was chromatographed over silica gel (40 g) eluting with a mixture of hexane and dichloromethane (3:1) to dichloromethane to give a colorless oil of (3S,4S)-1-(2-benzyloxy-4-fluorophenyl)-4-tert-butyldimethylsilyloxy-3-pentyl methanesulfonate (2.03 g, 80.2%).

EXAMPLE 60

The following compound was prepared in a similar manner to Example 1.

1-[(2S,3R)-5-(2-benzyloxy-4-fluorophenyl)-2-tert-butyldimethylsilyloxy-3-pentyl]imidazole-4-carboxamide (60)

NMR (CDCl$_3$, δ): −0.07(3H, s), −0.02(3H, s), 0.84(9H, s), 0.93(3H, d, J=6 Hz), 1.9–2.7(4H, m), 3.7–3.9(2H, m), 5.04(2H, s), 5.34(1H, s), 6.5–7.0(4H, m), 7.3–7.4(6H, m), 7.59(1H, d, J=1 Hz).

MS: 512(M+H)$^+$

EXAMPLE 61

1M solution of tetrabutylammonium fluoride in THF (1.22 ml) was added to a solution of 1-[(2S,3R)-5-(2-benzyloxy-4-fluorophenyl)-2-tert-butyldimethylsilyloxy-3-pentyl]imidazole-4-carboxamide (0.48 g) in THF (14 ml) and the mixture was stirred at room temperature for 2 hr.

EtOAc and water were added and the organic layer was washed with water twice, dried and evaporated. The residue (0.46 g) was chromatographed over silica gel (10 g) eluting with a mixture of dichloromethane and methanol (20:1 to 10:1) to give a pale brown powder of 1-[(2S,3R)-5-(2-benzyloxy-4-fluorophenyl)-2-hydroxy-3-pentyl]imidazole-4-carboxamide (61) (324 mg, 86.9%).

NMR (CDCl$_3$, δ): 1.03(3H, d, J=6 Hz), 1.82(1H, d, J=5 Hz), 2.0–2.7(4H, m), 3.8–4.0(2H, m), 5.04(2H, s), 5.35(1H, s), 6.5–7.0(4H, m), 7.3–7.5(6H, m), 7.65(1H, d, J=1 Hz).

MS: 398(M+H)$^+$

EXAMPLE 62

A mixture of 1-[(2S,3R)-5-(2-benzyloxy-4-fluorophenyl)-2-hydroxy-3-pentyl]imidazole-4-carboxamide (0.16 g) and 10% Pd—C (32 mg) in EtOAc (2 ml) and EtOH (2 ml) was stirred under hydrogen atmosphere at room temperature for 3 hr. Pd—C was removed by filtration and the filtrate was evaporated to give an off-white powder of 1-[(2S,3R)-5-(2-hydroxy-4-fluorophenyl)-2-hydroxy-3-pentyl]imidazole-4-carboxamide (62) (131 mg, 99%).

NMR (DMSO-d$_6$, δ): 0.90(3H, d, J=7 Hz), 1.9–2.4(4H, m), 3.7–4.0(2H, m), 5.09(1H, s), 6.5–6.7(2H, m), 6.9–7.1(2H, m), 7.30(1H, s), 7.73(2H, s), 9.89(1H, s).

MS: 308(M+H)$^+$

EXAMPLE 63

The following compound was prepared by a similar manner to Example 6-1.

1-{(2S,3R)-2-hydroxy-5-[4-fluoro-2-(4-(2-thienylthio)benzyloxy)phenyl]-3-pentyl}imidazole-4-carboxamide (63)

NMR (CDCl$_3$, δ): 1.02(3H, d, J=6 Hz), 1.9–2.6(5H, m), 3.7–4.0(2H, m), 4.96(2H, s), 5.37(1H, s), 6.5–7.6(12H, m), 7.64(1H, d, J=1 Hz).

MS: 512(M+H)$^+$

EXAMPLE 64

The following compound was prepared by a similar manner to Example 6-1.

1-{(2S,3R)-2-hydroxy-5-[2-(4-bromobenzyloxy)-4-fluorophenyl]-3-pentyl}imidazole-4-carboxamide (64)

NMR (CDCl$_3$, δ): 1.05(3H, d, J=6 Hz), 1.94(1H, d, J=5 Hz), 2.0–2.6(4H, m), 3.8–4.0(2H, m), 4.98(2H, s), 5.37(1H, s), 6.5–6.7(2H, m), 6.8–7.0(2H, m), 7.23(2H, d, J=8 Hz), 7.37(1H, d, J=1 Hz), 7.53(2H, d, J=8 Hz), 7.65(1H, d, J=1 Hz).

MS: 476, 478

EXAMPLE 65

The following compound was prepared in a similar manner to Example 1.

1-[(2S,3R)-5-(2-benzyloxy-4-chlorophenyl)-2-tert-butyldimethylsilyloxy-3-pentyl]imidazole-4-carboxamide (65)

NMR (CDCl$_3$, δ): −0.07(3H, s), −0.03(3H, s), 0.82(9H, s), 0.93(3H, d, J=6 Hz), 1.9–2.6(4H, m), 3.7–3.9(2H, m), 5.04(2H, s), 5.33(1H, s), 6.8–7.0(4H, m), 7.3–7.5(6H, m), 7.58(1H, d, J=1 Hz).

MS: 528(M+H)$^+$

EXAMPLE 66

The following compound was prepared in a similar manner to Example 61.

1-[(2S,3R)-5-(2-benzyloxy-4-chlorophenyl)-2-hydroxy-3-pentyl]imidazole-4-carboxamide (66)

NMR (CDCl$_3$, δ): 1.03(3H, d, J=6 Hz), 1.93(1H, d, J=5 Hz), 2.0–2.6(4H, m), 3.8–4.0(2H, m), 5.04(2H, s), 5.38(1H, s), 6.8–7.0(4H, m), 7.3–7.5(6H, m), 7.64(1H, d, J=1 Hz).

MS: 414(M+H)$^+$

EXAMPLE 67

The following compound was prepared in a similar manner to Example 62.

1-[(2S,3R)-5-(2-hydroxy-4-chlorophenyl)-2-hydroxy-3-pentyl]imidazole-4-carboxamide (67)

MS: 324(M+H)$^+$

EXAMPLE 68

The following compound was prepared in a similar manner to Example 6-1.

1-{(2S,3R)-2-hydroxy-5-[4-chloro-2-(5-bromo-2-thienylmethyloxy)phenyl]-3-pentyl}imidazole-4-carboxamide (68)

NMR (CDCl$_3$, δ): 1.06(3H, d, J=6 Hz), 1.88(1H, d, J=5 Hz), 2.0–2.6(4H, m), 3.8–4.0(2H, m), 5.12(2H, s), 5.40(1H, s), 6.8–7.0(6H, m), 7.39(1H, d, J=1 Hz), 7.65(1H, d, J=1 Hz).

MS: 498, 500

EXAMPLE 69

The following compound was prepared in a similar manner to Example 1.

1-[(2S,3R)-2-tert-butyldimethylsilyloxy-5-(2-phenoxyphenyl)-3-pentyl]imidazole-4-carboxamide (69)

MS: 480(M+H)$^+$

EXAMPLE 70

The following compound was prepared in a similar manner to Example 61.

1-[(2S,3R)-2-hydroxy-5-(2-phenoxyphenyl)-3-pentyl]imidazole-4-carboxamide hydrochloride (70)

NMR (DMSO-d$_6$, δ): 0.92(3H, d, J=6 Hz), 2.0–2.6(4H, m), 3.7–3.9(1H, m), 4.0–4.2(1H, m), 3.8–7.4(9H, m), 7.63 (1H, s), 7.93(1H, s), 8.10(1H, s), 8.69(1H, s).

MS: 366(M+H)$^+$

EXAMPLE 71

The following compound was prepared in a similar manner to Example 1.

1-[(2S,3R)-2-tert-butyldimethylsilyloxy-5-(2-(dimethylamino)phenyl)-3-pentyl]imidazole-4-carboxamide (71)

MS: 431(M+H)$^+$

EXAMPLE 72

The following compound was prepared in a similar manner to Example 61.

1-[(2S,3R)-2-hydroxy-5-(2-(dimethylamino)phenyl)-3-pentyl]imidazole-4-carboxamide (72)

NMR (CDCl$_3$, δ): 1.08(3H, d, J=6 Hz), 2.0–2.8(5H, m), 2.62(6H, s), 3.8–4.1(2H, m), 5.38(1H, s), 6.9–7.3(5H, m), 7.44(1H, d, J=1 Hz), 7.72(1H, d, J=1 Hz).

MS: 317(M+H)$^+$

Industrial Applicability

Novel imidazole compounds having pharmaceutical activity such as ADA inhibiting activity are provided. These compounds are useful in immunomodulation, especially immunosuppression, antiinflammation and treatment and prevention of various diseases for which Ado is effective. Such diseases include autoimmune diseases, inflammation, organ or tissue allo-or xeno-transplant rejection, leukemias, and diseases that arise from, or are aggravated by, insufficient blood flow through a particular organ or portion thereof. These compounds or their prodrugs or salts can be administered to patients in need of the treatment in an effective amount to elevate adenosine concentration.

What is claimed is:

1. A compound of the formula:

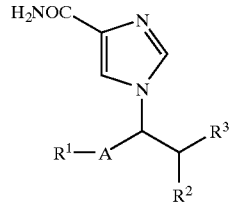

wherein R$^1$ is aryloxy, or aryl which is optionally substituted with substituent(s);

R$^2$ is lower alkyl;

R$^3$ is hydroxy or protected hydroxy; and

-A- is lower alkylene, or a salt thereof, or a prodrug thereof.

2. The compound according to claim 1, wherein R$^1$ is:

aryloxy, or aryl optionally substituted with substituent(s) selected from the group consisting of halogen; hydroxy; aryloxy; lower alkylthio; lower alkylsulfinyl; lower alkylsulfonyl; lower alkylamino; and lower alkoxy substituted with optionally substituted amino, protected amino, halogen, optionally substituted aryl, optionally substituted aryloxy, optionally substituted arylthio, optionally substituted arylsulfinyl, optionally substituted arylsulfonyl, optionally substituted aryl(lower) alkoxy, or optionally substituted heterocyclic group.

3. The compound according to claim 1, wherein R$^1$ is:

naphthyloxy;

phenyl substituted with substituent(s) selected from the group consisting of halogen, hydroxy, aryloxy, lower alkylthio, lower alkylsulfinyl, lower alkylsulfonyl, lower alkylamino, and lower alkoxy substituted with optionally substituted amino, protected amino, halogen, optionally substituted aryl, optionally substituted aryloxy, optionally substituted arylthio, optionally substituted arylsulfinyl, optionally substituted arylsulfonyl, optionally substituted aryl(lower)alkoxy, or optionally substituted heterocyclic group; or naphthyl substituted with halogen.

4. The compound according to any one of claims 2, wherein substituent(s) of the optionally substituted amino, optionally substituted aryl, optionally substituted aryloxy, optionally substituted arylthio, optionally substituted arylsulfinyl, optionally substituted arylsulfonyl, optionally substituted aryl(lower)alkoxy, or optionally substituted heterocyclic group, are each independently selected from the group consisting of aryl optionally substituted with halogen, lower alkyl or halo(lower)alkyl; halogen; aryloxy optionally substituted with halogen; heterocyclic group optionally substituted with cyano; aryloxy(lower)alkyl; aryl (lower)alkyl; aryl(lower)alkenyl; arylthio; lower cycloalkyl; lower alkylthio; heterocyclicthio optionally substituted with halogen; lower alkoxy; cyano; lower alkyl; halo(lower)alkyl; and amino optionally substituted with lower alkyl or lower alkanoyl.

5. The compound according to any one of claims 1, wherein A is ethylene.

6. The compound according to claim 1, wherein $R^1$ is aryloxy, or aryl which is optionally substituted with substituent(s);

$R^2$ is methyl;

$R^3$ is hydroxy; and

-A- is ethylene or a salt thereof.

7. The compound according to claim 1 selected from the group consisting of:

(1) 1-[(2S,3R)-2-benzyloxy-5-(2-(methylthio)phenyl)-3-pentyl]imidazole-4-carboxamide;

(2) 1-[(2S,3R)-2-hydroxy-5-(2-(methylthio)phenyl)-3-pentyl]imidazole-4-carboxamide;

(3) 1-[(2S,3R)-2-hydroxy-5-(2-(methylsulfinyl)phenyl)-3-pentyl]imidazole-4-carboxamide;

(4) 1-[(2S,3R)-2-hydroxy-5-(2-(methylsulfonyl)phenyl)-3-pentyl]imidazole-4-carboxamide;

(5) 1-{(2S,3R)-2-hydro):y-5-[2-(3-dimethylaminopropoxy)phenyl]3-pentyl}imidazole-4-carboxamide dihydrochloride;

(6-1) 1-{(2S,3R)-2-hydroxy-5-[2-(6-phthalimidohexyloxy)phenyl]-3-pentyl}imidazole-4-carboxamide;

(6-2) 1-{(2S,3R)-2-hydroxy-5-[2-(6-aminohexyloxy)phenyl]-3-pentyl}imidazole-4-carboxamide dihydrochloride;

(7) 1-{(2S,3R)-2-hydroxy-5-[2-(2,2,2-trifluoroethoxy)phenyl]-3-pentyl}imidazole-4-carboxamide;

(8) 1-{(2S,3R)-2-hydroxy-5-[2-(3-(4-chlorophenyl)propoxy)-phenyl]-3-pentyl}imidazole-4-carboxamide;

(9) 1-[(2S,3R)-2-benzyloxy-5-(6-chloro-1-naphthyl)-3-pentyl]imidazole-4-carboxamide;

(10) 1-[(2S,3R)-2-hydroxy-5-(6-chloro-1-naphthyl)-3-pentyl]imidazole-4-carboxamide;

(11) 1-[(2S,3R)-2-benzyloxy-5-(7-chloro-1-naphthyl)-3-pentyl]imidazole-4-carboxamide;

(12) 1-[(2S,3R)-2-hydroxy-5-(7-chloro-1-naphthyl)-3-pentyl]imidazole-4-carboxamide;

(13) 1-[(2S,3R)-2-benzyloxy-5-(1-naphthyloxy)-3-pentyl]imidazole-4-carboxamide;

(14) 1-[(2S,3R)-2-hydroxy-5-(1-naphthyloxy)-3-pentyl] imidazole-4-carboxamide;

(15) 1-[(2S,3R)-2-benzyloxy-5-(2-naphthyloxy)-3-pentyl]imidazole-4-carboxamide;

(16) 1-[(2S,3R)-2-hydroxy-5-(2-naphthyloxy)-3-pentyl] imidazole-4-carboxamide;

(17) 1-[(2S,3R)-2-hydroxy-5-(2,3-dichlorophenyl)-3-pentyl]imidazole-4-carboxamide hydrochloride;

(18) 1-{(2S,3R)-2-hydroxy-5-[2-(2-(4-chlorophenoxy)ethoxy)phenyl]-3-pentyl}imidazole-4-carboxamide hydrochloride;

(19) 1-{(2S,3R)-2-hydroxy-5-[2-(2-(4-chlorophenylthio)ethoxy)phenyl]3-pentyl}imidazole-4-carboxamide;

(20) 1-{(2S,3R)-2-hydroxy-5-[2-(2-(4-chlorophenylsulfonyl)ethoxy)phenyl]-3-pentyl}imidazole-4-carboxamide;

(21) 1-{(2S,3R)-2-hydroxy-5-[2-(2-(3,4-dichlorobenzyloxy)ethoxy)phenyl]-3-pentyl}imidazole-4-carboxamide;

(22) 1-{(2S,3R)-2-hydroxy-5-[2-(4-phenylbenzyloxy)phenyl]-3-pentyl}imidazole-4-carboxamide;

(23) 1-{(2S,3R)-2-hydroxy-5-[2-(3,4-dichlorobenzyloxy)phenyl]-3-pentyl}imidazole-4-carboxamide;

(24) 1-{(2S,3R)-2-hydroxy-5-[2-(4-phenoxybenzyloxy)phenyl]-3-pentyl}imidazole-4-carboxamide;

(25) 1-{(2S,3R)-2-hydroxy-5-[2-(2-naphthylmethyloxy)phenyl]-3-pentyl}imidazole-4-carboxamide;

(26) 1-{(2S,3R)-2-hydroxy-5-[2-(4-(1-methyl-1-phenylethyl)benzyloxy)phenyl]-3-pentyl}imidazole-4-carboxamide;

(27) 1-{(2S,3R)-2-hydroxy-5-[2-(4-(2-pyridyl)benzyloxy)phenyl]-3-pentyl}imidazole-4-carboxamide;

(28) 1-{(2S,3R)-2-hydroxy-5-[2-(4-(4-fluorophenoxy)benzyloxy)phenyl]3-pentyl}imidazole-4-carboxamide;

(29) 1-{(2S,3R)-2-hydroxy-5-[2-(3-(phenoxymethyl)benzyloxy)phenyl]-3-pentyl}imidazole-4-carboxamide;

(30) 1-{(2S,3R)-2-hydroxy-5-[2-(4-isopropylbenzyloxy)phenyl]-3-pentyl}imidazole-4-carboxamide;

(31) 1-{(2S,3R)-2-hydroxy-5-[2-(4-(2-cyano-1-pyrrolyl)-3-fluorobenzyloxy)phenyl]-3-pentyl}imidazole-4-carboxamide;

(32) 1-{(2S,3R)-2-hydroxy-5-[2-(5-(4-tert-butylphenyl)-1,2,4-oxadiazol-3-ylmethyloxy)phenyl]-3-pentyl}imidazole-4-carboxamide;

(33) 1-{(2S,3R)-2-hydroxy-5-[2-(4-chlorobenzyloxy)phenyl]-3-pentyl}imidazole-4-carboxamide hydrochloride;

(34) 1-{(2S,3R)-2-hydroxy-5-[2-(4-bromobenzyloxy)phenyl]-3-pentyl}imidazole-4-carboxamide hydrochloride;

(35) 1-{(2S,3R)-2-hydroxy-5-[2-(4-(E)-styrylbenzyloxy)phenyl]-3-pentyl}imidazole-4-carboxamide hydrochloride;

(36) 1-{(2S,3R)-2-hydroxy-5-[2-(4-phenylthiobenzyloxy)phenyl]-3-pentyl}imidazole-4-carboxamide hydrochloride;

(37) 1-{(2S,3R)-2-hydroxy-5-[2-(4-cyclohexylbenzyloxy)phenyl]-3-pentyl}imidazole-4-carboxamide hydrochloride;

(38) 1-{(2S,3R)-2-hydroxy-5-[2-(2-(4-(trifluoromethyl)phenyl)-4-thiazolylmethyloxy)phenyl]-3-pentyl}imidazole-4-carboxamide;

(39) 1-{(2S,3R)-2-hydroxy-5-[2-(4-(methylthio)benzyloxy)phenyl]-3-pentyl}imidazole-4-carboxamide hydrochloride;

(40) 1-{(2S,3R)-2-hydroxy-5-[2-(3-bromobenzyloxy)phenyl]-3-pentyl}imidazole-4-carboxamide hydrochloride;

(41) 1-{(2S,3R)-2-hydroxy-5-[2-(4-bromo-2-fluorobenzyloxy)phenyl]-3-pentyl}imidazole-4-carboxamide hydrochloride;

(42) 1-{(2S,3R)-2-hydroxy-5-[2-(4-(1,2,3-thiadiazol-4-yl)benzyloxy)phenyl]-3-pentyl}imidazole-4-carboxamide;

(43) 1-{(2S,3R)-2-hydroxy-5-[2-(2-(N-methylpropionylamino)-4-thiazolylmethyloxy)phenyl]-3-pentyl}imidazole-4-carboxamide;

(44) 1-{(2S,3R)-2-hydroxy-5-[2-(4-(2-thienylthio)benzyloxy)phenyl]-3-pentyl}imidazole-4-carboxamide hydrochloride;

(45) 1-{(2S,3R)-2-hydroxy-5-[2-(4-(5-chloro-2-thienylthio)benzyloxy)phenyl]-3-pentyl}imidazole-4-carboxamide hydrochloride;

(46) 1-{(2S,3R)-2-hydroxy-5-[2-(4-(2-thienyl)benzyloxy)phenyl]-3-pentyl}imidazole-4-carboxamide;

(47) 1-{(2S,3R)-2-hydroxy-5-[2-(4-methoxybenzyloxy)phenyl]-3-pentyl}imidazole-4-carboxamide hydrochloride;

(48) 1-{(2S,3R)-2-hydroxy-5-[2-(4-(3-thienyl)-2-thienylmethyloxy)phenyl]-3-pentyl}imidazole-4-carboxamide hydrochloride;

(49) 1-{(2S,3R)-2-hydroxy-5-[2-(4-cyanobenzyloxy)phenyl]-3-pentyl}imidazole-4-carboxamide;

(50) 1-{(2S,3R)-2-hydroxy-5-[2-(3,5-dibromobenzyloxy)phenyl]-3-pentyl}imidazole-4-carboxamide hydrochloride;

(51) 1-{(2S,3R)-2-hydroxy-5-[2-(5-bromo-2-thienylmethyloxy)phenyl]-3-pentyl}imidazole-4-carboxamide hydrochloride;

(52) 1-{(2S,3R)-2-hydroxy-5-[2-(5-(4-fluorophenyl)-2-thienylmethyloxy)phenyl]-3-pentyl}imidazole-4-carboxamide hydrochloride;

(53) 1-{(2S,3R)-2-hydroxy-5-[2-(3,5-bis(trifluoromethyl)benzyloxy)phenyl]-3-pentyl}imidazole-4-carboxamide hydrochloride;

(54) 1-{(2S,3R)-2-hydroxy-5-[2-(3,5-dimethoxybenzyloxy)phenyl]-3-pentyl}imidazole-4-carboxamide hydrochloride;

(55) 1-{(2S,3R)-2-hydroxy-5-[2-(2-(4-biphenylyloxy)ethyloxy)phenyl]-3-pentyl}imidazole-4-carboxamide hydrochloride;

(56) 1-{(2S,3R)-2-hydroxy-5-[2-(5-(2-thiazolylthio)-2-thienylmethyloxy)phenyl]-3-pentyl}imidazole-4-carboxamide;

(57) 1-{(2S,3R)-2-hydroxy-5-[2-(4-ethoxybenzyloxy)phenyl]-3-pentyl}imidazole-4-carboxamide hydrochloride;

(58) 1-{(2S,3R)-2-hydroxy-5-[2-(2-(4-biphenylyl)ethyloxy)phenyl]-3-pentyl}imidazole-4-carboxamide;

(59) 1-{(2S,3R)-2-hydroxy-5-[2-(3,5-dimethylbenzyloxy)phenyl]-3-pentyl}imidazole-4-carboxamide;

(60) 1-[(2S,3R)-5-(2-benzyloxy-4-fluorophenyl)-2-tert-butyldimethylsilyloxy-3-pentyl]imidazole-4-carboxamide;

(61) 1-[(2S,3R)-5-(2-benzyloxy-4-fluorophenyl)-2-hydroxy-3-pentyl]imidazole-4-carboxamide;

(62) 1-[(2S,3R)-5-(2-hydroxy-4-fluorophenyl)-2-hydroxy-3-pentyl]imidazole-4-carboxamide;

(63) 1-{(2S,3R)-2-hydroxy-5-[4-fluoro-2-(4-(2-thienylthio)benzyloxy)phenyl]-3-pentyl}imidazole-4-carboxamide;

(64) 1-{(2S,3R)-2-hydroxy-5-[2-(4-bromobenzyloxy)-4-fluorophenyl]-3-pentyl}imidazole-4-carboxamide;

(65) 1-[(2S,3R)-5-(2-benzyloxy-4-chlorophenyl)-2-tert-butyldimethylsilyloxy-3-pentyl]imidazole-4-carboxamide;

(66) 1-[(2S,3R)-5-(2-benzyloxy-4-chlorophenyl)-2-hydroxy-3-pentyl]imidazole-4-carboxamide;

(67) 1-[(2S,3R)-5-(2-hydroxy-4-chlorophenyl)-2-hydroxy-3-pentyl]imidazole-4-carboxamide;

(68) 1-{(2S,3R)-2-hydroxy-5-[4-chloro-2-(5-bromo-2-thienylmethyloxy)phenyl]-3-pentyl}imidazole-4-carboxamide;

(69) 1-[(2S,3R)-2-tert-butyldimethylsilyloxy-5-(2-phenoxyphenyl)-3-pentyl]imidazole-4-carboxamide;

(70) 1-[(2S,3R)-2-hydroxy-5-(2-phenoxyphenyl)-3-pentyl]imidazole-4-carboxamide hydrochloride;

(71) 1-[(2S,3R)-2-tert-butyldimethylsilyloxy-5-(2-(dimethylamino)phenyl)-3-pentyl]imidazole-4-carboxamide; and

(72) 1-[(2S,3R)-2-hydroxy-5-(2-(dimethylamino)phenyl)-3-pentyl]imidazole-4-carboxamide.

8. The compound according to claim 1, selected from the group consisting of:

(8) 1-{(2S,3R)-2-hydroxy-5-[2-(3-(4-chlorophenyl)propoxy)-phenyl]-3-pentyl}imidazole-4-carboxamide;

(10) 1-[(2S,3R)-2-hydroxy-5-(6-chloro-1-naphthyl)-3-pentyl]imidazole-4-carboxamide;

(16) 1-[(2S,3R)-2-hydroxy-5-(2-naphthyloxy)-3-pentyl]imidazole-4-carboxamide;

(18) 1-{(2S,3R)-2-hydroxy-5-[2-(2-(4-chlorophenoxy)ethoxy)phenyl]-3-pentyl}imidazole-4-carboxamide hydrochloride;

(19) 1-{(2S,3R)-2-hydroxy-5-[2-(2-(4-chlorophenylthio)ethoxy)phenyl]3-pentyl}imidazole-4-carboxamide;

(44) 1-{(2S,3R)-2-hydroxy-5-[2-(4-(2-thienylthio)benzyloxy)phenyl]-3-pentyl}imidazole-4-carboxamide hydrochloride;

(50) 1-{(2S,3R)-2-hydroxy-5-[2-(3,5-dibromobenzyloxy)phenyl]-3-pentyl}imidazole-4-carboxamide hydrochloride;

(51) 1-{(2S,3R)-2-hydroxy-5-[2-(5-bromo-2-thienylmethyloxy)phenyl]-3-pentyl}imidazole-4-carboxamide hydrochloride;

(54) 1-{(2S,3R)-2-hydroxy-5-[2-(3,5-dimethoxybenzyloxy)phenyl]-3-pentyl}imidazole-4-carboxamide hydrochloride; and

(57) 1-{(2S,3R)-2-hydroxy-5-[2-(4-ethoxybenzyloxy)phenyl]-3-pentyl}imidazole-4-carboxamide hydrochloride.

9. A pharmaceutical composition comprising:

the compound of claim 1 and a pharmaceutically acceptable carrier or excipient.

10. A pharmaceutical composition having an adenosine deaminase inhibiting activity, which comprises:

the compound of claim 1 and a pharmaceutically acceptable carrier or excipient.

11. A method for inhibiting adenosine deaminase activity (ADA) or for elevating adenosine concentration, which comprises administering the compound of claim 1 to a mammal.

12. A process for producing the compound of claim 1, comprising any of the following steps (1) to (4):

(1) reacting a compound of formula (III):

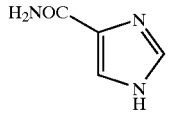

(III)

with a compound of formula (IV):

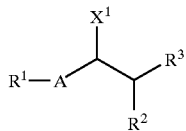

(IV)

wherein $R^1$, $R^2$, $R^3$, and A are as defined above, and $X^1$ is hydroxy or a leaving group, provided that $R^3$ is not hydroxy;

(2) reacting a compound of formula (V):

$R^1$—OH   (V)

wherein $R^1$ is as defined above, with a compound of formula (VI):

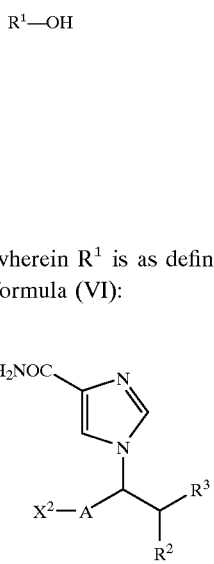

(VI)

wherein $R^2$, $R^3$, and A are as defined above, and $X^2$ is hydroxy or a leaving group, provided that $R^3$ is not hydroxy;

(3) reacting a compound of formula (I-1):

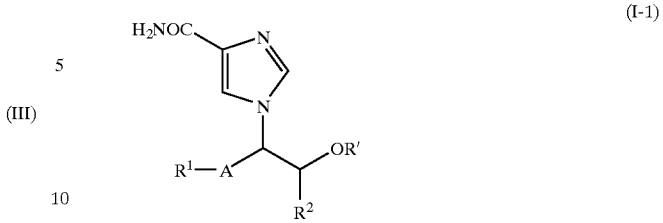

(I-1)

wherein $R^1$, $R^2$, and A are as defined above, and $R^2$ is hydroxy protective group, with a deprotecting agent; or (4) reacting a compound of formula (VII):

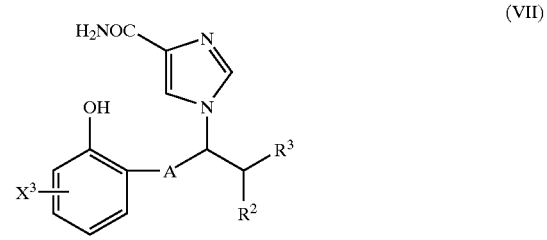

(VII)

wherein $R^2$ and $R^3$ are as defined above and $X^3$ is hydrogen or halogen, with a compound of formula (VIII):

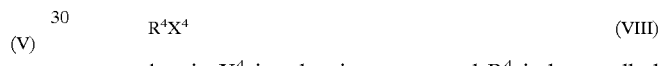

$R^4X^4$   (VIII)

wherein $X^4$ is a leaving group and $R^4$ is lower alkyl substituted with optionally substituted amino, protected amino, halogen, optionally substituted aryl, optionally substituted aryloxy, optionally substituted arylthio, optionally substituted arylsulfinyl, optionally substituted arylsulfonyl, optionally substituted aryl(lower) alkoxy or optionally substituted heterocyclic group; wherein substituent(s) of the optionally substituted amino, optionally substituted aryl, optionally substituted aryloxy, optionally substituted arylthio, optionally substituted arylsulfinyl, optionally substituted arylsulfonyl, optionally substituted aryl(lower)alkoxy, and optionally substituted heterocyclic group, are each independently selected from the group consisting of aryl optionally substituted with halogen, lower alkyl or halo(lower)alkyl; halogen; aryloxy optionally substituted with halogen; aryl(lower)alkyl; heterocyclic group optionally substituted with cyano; aryloxy (lower)alkyl; aryl(lower)alkenyl; arylthio; lower cycloalkyl; lower alkylthio; heterocyclicthio optionally substituted with halogen; lower alkoxy; cyano; lower alkyl; halo(lower)alkyl; and amino optionally substituted with lower alkyl or lower alkanoyl.

13. A method for for preparing a composition comprising admixing the compound of claim 1 with a pharmaceutically acceptable excipient or carrier.

* * * * *

UNITED STATES PATENT AND TRADEMARK OFFICE
CERTIFICATE OF CORRECTION

PATENT NO. : 6,908,940 B2
DATED : June 21, 2005
INVENTOR(S) : Tsuji et al.

It is certified that error appears in the above-identified patent and that said Letters Patent is hereby corrected as shown below:

<u>Title page,</u>
Insert Items -- [45] **Date of Patent: \*Jun. 21, 2005**

[\*] Notice: Subject to any disclaimer, the term of this patent is extended or adjusted under 35 U.S.C. 154(b) by 207 days.

This patent is subject to a terminal disclaimer. --.

Signed and Sealed this

Sixth Day of September, 2005

JON W. DUDAS
*Director of the United States Patent and Trademark Office*